US007056716B2

(12) United States Patent
Potter et al.

(10) Patent No.: US 7,056,716 B2
(45) Date of Patent: *Jun. 6, 2006

(54) HIGH FIDELITY REVERSE TRANSCRIPTASES AND USES THEREOF

(75) Inventors: Robert Jason Potter, Frederick, MD (US); Kim Rosenthal, Laytonsville, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/808,124

(22) Filed: Mar. 15, 2001

(65) Prior Publication Data

US 2003/0003452 A1    Jan. 2, 2003

Related U.S. Application Data

(60) Provisional application No. 60/189,454, filed on Mar. 15, 2000.

(51) Int. Cl.
| | |
|---|---|
| C12N 9/12 | (2006.01) |
| C12N 9/00 | (2006.01) |
| C12P 19/34 | (2006.01) |
| C12Q 1/68 | (2006.01) |

(52) U.S. Cl. ............... 435/194; 435/183; 435/91.1; 435/6

(58) Field of Classification Search ............... 435/6, 435/91.1, 183, 194
See application file for complete search history.

(56) References Cited

U.S. PATENT DOCUMENTS

| 5,244,797 A | 9/1993 | Kotewicz et al. ........... 435/194 |
| 5,405,776 A | 4/1995 | Kotewicz et al. ...... 435/252.33 |
| 5,668,005 A | 9/1997 | Kotewicz et al. ........... 435/194 |
| 6,063,608 A | 5/2000 | Kotewicz et al. ........... 435/194 |
| 6,136,582 A | 10/2000 | Gao et al. ................. 435/194 |
| 6,306,588 B1 | 10/2001 | Solus et al. | 
| 6,395,524 B1 | 5/2002 | Loeb et al. | 
| 2001/0012613 A1 | 8/2001 | Loeb et al. ..................... 435/6 |

FOREIGN PATENT DOCUMENTS

| JP | 2000-139457 | 5/2000 |
| WO | WO 98/47912 | 10/1998 |
| WO | WO 99/10366 | 3/1999 |

OTHER PUBLICATIONS

Halvas, E.K. et al., "Development of an In Vivo Assay To identify Structural Determinants in Murine Leukemia Virus Reverse Transcriptase Important for Fidelity", J. Virology, vol. 74, pp. 312-319, Jan. 1999.*
Pfeiffer, J. K. et al., "Structure-Based Moloney Murine Leukemia Virus Reverse Transcriptase Mutants with Altered Intracellular Direct-Repeat Deletion Frequencies", J. Virol., vol. 74, pp. 9629-9636, Oct. 2000.*

Hizi, A. et al., "Mutational Analysis of the Ribonuclease H activity of Human Immunodeficiency Virus 1 Reverse Transcriptase", Virology, vol. 175, pp. 575-580 (1990).*
Schatz, O. et al., "Point mutations in conserved amino acid residues within the C-terminal domain of HIV-1 reverse transcriptas specifically repress RNase H function", FEBS Letters, vol. 257, pp. 311-314 (1989).*
Allain, B., et al., "*CIS* Elements and *Trans*-acting Factors required for Minus Strand DNA Transfer during Reverse Transcription of the Genomic RNA of Murine Leukemia Virus," *J. Mol. Biol.* 277:225-235, Academic Press(1998).
Arian, D., et al., "The K65R Mutation Confers Increased DNA Polymerase Processivity to HIV-1 Reverse Transcriptase," *J. Biol. Chem.* 271:19860-19864, American Society for Biochemistry and Molecular Biology (1996).
Arnold, E., et al., "Targeting HIV Reverse Transcriptase for Anti-AIDS Drug Design: Structural and Biological Considerations for Chemotherapeutic Strategies," *Drug Design and Discovery* 13:29-47, Harwood Academic Publishers GmbH (1996).
Bahar, I., et al., "Collective Motions in HIV-1 Reverse Transcriptase: Examination of Flexibility and Enzyme Function," *J. Mol. Biol.* 285:1023-1037, Academic Press (Jan. 1999).
Bakhanashvili, M., and Hizi, A., "A possible role for cysteine residues in the fidelity of DNA synthesis exhibited by the reverse transcriptase of human immunodeficiency viruses type 1 and type 2," *FEBS* 304:289-293, Elsevier Science Publishers B.V. (1992).
Bakhanashvili, M., and Hizi, A., "Fidelity of the reverse transcriptase of human immunodeficiency virus type 2," *FEBS* 306:151-156, Elsevier Science Publishers B.V. (1992).
Bakhanashvili, M., and Hizi, A., "Fidelity of the RNA-Dependent DNA Synthesis Exhibited by the Reverse Transcriptases of Human Immunodeficiency Virus Types 1 and 2 and of Murine Leukemia Virus: Mispair Extension Frequencies," *Biochem.* 31:9393-9398, American Chemical Society (1992).

(Continued)

Primary Examiner—Jeffrey Fredman
Assistant Examiner—Teresa Strzelecka
(74) Attorney, Agent, or Firm—Sterne, Kessler, Goldstein & Fox PLLC

(57) ABSTRACT

The invention relates to reverse transcriptases which have increased fidelity (or reduced misincorporation rate) and/or terminal deoxynucleotidyl transferase activity. In particular, the invention relates to a method of making such reverse transcriptases by modifying or mutating specified positions in the reverse transcriptases. The invention also relates to nucleic acid molecules containing the genes encoding the reverse trancriptases of the invention, to host cells containing such nucleic acid molecules and to methods to make the reverse transcriptases using the host cells. The reverse tran- scriptases of the invention are particularly suited for nucleic acid synthesis, sequencing, amplification and cDNA synthesis.

22 Claims, 10 Drawing Sheets

OTHER PUBLICATIONS

Bakhanashvili, M., and Hizi, A., "The fidelity of the reverse transcriptases of human immunodeficiency viruses and murine leukemia virus, exhibited by the mispair extension frequencies, is sequence dependent and enzyme related," *FEBS 319*:201-205, Elsevier Science Publishers B.V. (1993).

Bakhanashvili, M., et al., "Mutational studies of human immunodeficiency virus type 1 reverse transcriptase: the involvement of residues 183 and 184 in the fidelity of DNA synthesis," *FEBS Lett. 391*:257-262, Elsevier Science Publishers B.V. (1996).

Basu, S., et al., "Sulphydryl groups in the template-primer-binding domain of murine leukemia virus reverse transcriptase," *Biochem. J. 296*:577-583, The Biochemical Society, London (1993).

Beard, W.A., et al., "Structure/Function Studies of Human Immunodeficiency Virus Type 1 Reverse Transcriptase," *J. Biol. Chem. 269*:28091-28097, American Society for Biochemistry and Molecular Biology (1994).

Beard, W.A., et al., "Vertical-scanning Mutagenesis of a Critical Tryptophan in the Minor Groove Binding Track of HIV-1 Reverse Transcriptase," *J. Biol. Chem. 273*:30435-30442, American Society for Biochemistry and Molecular Biology (1998).

Bebenek, K., and Kunkel, T.A., "The Fidelity of Retroviral Reverse Transcriptase," in *Reverse Transcriptase*, Skalka, A.M., and Goff, S.P. (eds.), Cold Spring Harbor Laboratory Press, Plainview, NY, pp. 85-102 (1993).

Bebenek, K., et al., "Specificity and Mechanism of Error-prone Replication by Human Immunodeficiency Virus-1 Reverse Transcriptase," *J. Biol. Chem. 264*:16948-16956, American Society for Biochemistry and Molecular Biology (1989).

Bebenek, K., et al., "The Effects of dNTP Pool Imbalances on Frameshift Fidelity during DNA Replication," *J. Biol. Chem. 267*:3589-3596, American Society for Biochemistry and Molecular Biology (1992).

Bebenek, K., et al., "Error-prone Polymerization by HIV-1 Reverse Transcriptase," *J. Biol. Chem. 268*:10324-10334, American Society for Biochemistry and Molecular Biology (1993).

Bebenek, K., and Kunkel, T.A., "Analyzing Fidelity of DNA Polymerases," *Methods in Enzymol. 262*:217-232, Academic Press (1995).

Bebenek, K., et al., "Reduced Frameshift Fidelity and Processivity of HIV-1 Reverse Transcriptase Mutants Containing Alanine Substitutions in Helix H of the Thumb Subdomain," *J. Biol. Chem. 270*:19516-19523, American Society for Biochemistry and Molecular Biology (1995).

Bebenek, K., et al., "A minor groove binding track in reverse transcriptase," *Nature Structural Biol. 4*:194-197, Macmillan Magazines Ltd (1997).

Ben-Artzi, H., et al., "Characterization of the double stranded RNA dependent RNase activity associated with recombinant reverse transcriptase," *Nucleic Acids Res. 20*:5115-5118, Oxford University Press (1992).

Blain, S.W., and Goff, S.P., "Effects on DNA Synthesis and Translocation Caused by Mutations in the RNase H Domain of Moloney Murine Leukemia Virus Reverse Transcriptase," *J. Virol. 69*:4440-4452, The American Society for Microbiology (1995).

Boyer, J.C., et al., "Analyzing the Fidelity of Reverse Transcription and Transcription," *Meth. in Enzymol. 275*:523-537, Academic Press (1996).

Boyer, P.L., et al., "Mutational Analysis of the Fingers Domain of Human Immunodeficiency Virus Type 1 Reverse Transcriptase," *J. Virol. 66*:7533-7537, The American Society for Microbiology (1992).

Boyer, P.L., et al., "Mutational Analysis of the Fingers and Palm Subdomains of Human Immunodeficiency Virus Type-1 (HIV-1) Reverse Transcriptase," *J. Mol. Biol. 243*:472-483, Academic Press (1994).

Boyer, P.L., and Hughes, S.H., "Analysis of Mutations at Position 184 in Reverse Transcriptase of Human Immunodeficiency Virus Type 1," *Antimicrobial Agents and Chemotherapy 39*:1624-1628, The American Society for Microbiology (1995).

Caliendo, A.M., et al., "Effects of Zidovudine-Selected Human Immunodeficiency Virus Type 1 Reverse Transcriptase Amino Acid Substitutions on Processive DNA Synthesis and Viral Replication," *J. Virol. 70*:2146-2153, The American Society for Microbiology (1996).

Catucci, M., et al., "Development and Significance of the HIV-1 Reverse Transcriptase M184V Mutation During Combination Therapy With Lamivudine, Zidovudine, and Protease Inhibitors," *J. Acquired Immune Deficiency Syndromes 21*:203-208, Lippincott Williams & Wilkins, Inc. (Jul. 1999).

Chao, S-F., et al., "Mutational sensitivity patterns define critical residues in the palm subdomain of the reverse transcriptase of human immunodeficiency virus type 1," *Nucleic Acids Res. 23*:803-810, Oxford University Press (1995).

Chen, Y., and Marion, P.L., "Amino Acids Essential for RNase H Activity of Hepadnaviruses Are Also Required for Efficient Elongation of Minus-Strand Viral DNA," *J. Virol. 70*:6151-6156, The American Society for Microbiology (1996).

Chowdhury, K., et al., "Elucidation of the Role of Arg 110 of Murine Leukemia Virus Reverse Transcriptase in the Catalytic Mechanism: Biochemical Characterization of Its Mutant Enzymes," *Biochemistry 35*:16610-16620, American Chemical Society (1996).

Creighton, S., et al., "Base Mispair Extension Kinetics," 267:2633-2639, American Society for Biochemistry and Molecular Biology (1992).

DeStefano, J.J., et al., "Parameters that influence processive synthesis and site-specific termination by human immunodeficiency virus reverse transcriptase on RNA and DNA templates," *Biochimica et Biophysica Acta 1131*:270-280, Elsevier Science Publishers B.V. (1992).

Diaz, L., and DeStefano, J.J., "Strand transfer is enhanced by mismatched nucleotides at the 3' primer terminus: a possible link between HIV reverse transcriptase fidelity and recombination," *Nucleic Acids Res. 24*:3086-3092, Oxford University Press (1996).

Drosopoulos, W.C., and Prasad, V.R., "Increased Polymerase Fidelity of E89G, a Nucleoside Analog-Resistant Variant of Human Immunodeficiency Virus Type 1 Reverse Transcriptase," *J. Virol. 70*:4834-4838, The American Society for Microbiology (1996).

Drosopoulos, W.C., and Prasad, V.R., "Increased Misincorporation Fidelity Observed for Nucleoside Analog Resistance Mutations M184V and E89G in Human Immunodeficiency Virus Type 1 Reverse Transcriptase Does Not Correlate with the Overall Error Rate Measured In Vitro," *J. Virol. 72*:4224-4230, The American Society for Microbiology (1998).

Dudding, L.R., et al., "Analysis of the RNA- and DNA-Dependent DNA Polymerase Activities of Point Mutants of HIV-1 Reverse Transcriptase Lacking Ribonuclease H Activity," *Biochemistry 30*:10498-10506, American Chemical Society (1991).

Eckert, K.A., and Kunkel, T.A., "Fidelity of DNA synthesis catalyzed by human DNA polymerase α and HIV-1 reverse transcriptase: effect of reaction pH," *Nucleic Acids Res. 21*:5212-5220, Oxford University Press (1993).

Feng, J.Y., and Anderson, K.S., "Mechanistic Studies Examining the Efficiency and Fidelity of DNA Synthesis by the 3TC-Resistant Mutant (184V) of HIV-1 Reverse Transcriptase," *Biochemistry 38*:9440-9448, The American Chemical Society (Jul. 1999; published on the web Jun. 30, 1999).

Gao, G., and Goff, S.P., "Replication Defect of Moloney Murine Leukemia Virus with a Mutant Reverse Transcriptase That Can Incorporate Ribonucleotides and Deoxyribonucleotides," *J. Virol. 72*:5905-5911, The American Society for Microbiology (1998).

Gao, G., et al., "Conferring RNA polymerase Activity to a DNA polymerase: A single residue in reverse transcriptase controls substrate selection," *Proc. Natl. Acad. Sci. USA 94*:407-411, The National Academy of Sciences of the USA (1997).

Georgiadis, M.M., et al., "Mechanistic implications from the structure of a catalytic fragment of Moloney murine leukemia virus reverse transcriptase," *Structure 3*:879-892, Current Biology Ltd (1995).

Gerard, G.F., and D'Alessio, J.M., "Reverse Transcriptase (EC 2.7.7.49),"*Methods in Molecular Biol. 16*:73-93, Humana Press (1993).

Goff, S.P., "Retroviral Reverse Transcriptase: Synthesis, Structure, and Function," *J. Acquired Immune Deficiency Syndrome 3*:817-831, Raven Press (1990).

Goobar-Larsson, L., et al., "Disruption of a Salt Bridge between Asp 488 and Lys 465 in HIV-1 Reverse Transcriptase Alters Its Proteolytic Processing and Polymerase Activity," *Virology 196*:731-738, Academic Press (1993).

Götte, M., et al., "The M184V Mutation in the Reverse Transcriptase of Human Immunodeficiency Virus Type 1 Impairs Rescue of Chain-Terminated DNA Synthesis," *J. Virol. 74*:3579-3585, The American Society for Microbiology (Apr. 2000).

Guo, J., et al., "Defects in Primer-Template Binding, Processive DNA Synthesis, and RNase H Activity Associated with Chimeric Reverse Transcriptases Having the Murine Leukemia Virus Polymerase Domain Joined to *Escherichia coli* RNase H," *Biochemistry 34*:5018-5029, The American Chemical Society (1995).

Gutiérrez-Rivas, M., et al., "Mutational Analysis of Phe160 within the "Palm" Subdomain of Human Immunodeficiency Virus Type 1 Reverse Transcriptase," *J. Mol. Biol. 290*:615-625, Academic Press (Jul. 1999).

Hamburgh, M.E., et al., "The influence of 3TC-resistance mutations E89G and M184V in the human immunodeficiency virus reverse transcriptase on mispair extension efficiency," *Nucleic Acids Res. 26*:4389-4394, Oxford University Press (1998).

Harris, D., et al., "Loss of Polymerase Activity Due to Tyr to Phe Substitution in the YMDD Motif of Human Immunodeficiency Virus Type-1 Reverse Transcriptase Is Compensated by Met to Val Substitution with the Same Motif," *Biochemistry 37*:9630-9640, The American Chemical Society (1998).

Harris, D., et al., "Functional Analysis of Amino Acid Residues Constituting the dNTP Binding Pocket of HIV-1 Reverse Transcriptase," *J. Biol. Chem. 273*:33624-33634, American Society for Biochemistry and Molecular Biology (1998).

Hizi, A., and Hughes, S.H., "Expression in *Escherichia coli* of a Moloney murine leukemia virus reverse transcriptase whose structure closely resembles the viral enzyme," *Gene 66*:319-323, Elsevier Science Publishers B.V. (1988).

Hizi, A., et al., "Catalytic Properties of the Reverse Transcriptase of Human Immunodeficiency Viruses Type 1 and Type 2," *J. Biol. Chem. 226*:6230-6239, The American Society for Biochemistry and Molecular Biology (1991).

Hsu, M., et al., "Higher fidelity of RNA-dependent DNA mispair extension by M184V drug-resistant than wild-type reverse transcriptase of human immunodeficiency virus type 1," *Nucleic Acids Research 25*:4532-4536, Oxford University Press (1997).

Hübner, A., et al., "Fidelity of Human Immunodeficiency Virus Type I Reverse Transcriptase in Copying Natural RNA," *J. Mol. Biol. 223*:595-600, Academic Press (1992).

Ji, J., and Loeb, L.A., "Fidelity of HIV-1 Reverse Transcriptase Copying RNA in Vitro," *Biochemistry 31*:954-958, The American Chemical Society (1992).

Jin, J., et al., "Analysis of the Role of Glutamine 190 in the Catalytic Mechanism of Murine Leukemia Virus Reverse Transcriptase," *J. Biol. Chem. 274*:20861-20868, American Society for Biochemistry and Molecular Biology (Jul. 1999).

Kanda, T., and Saigo, K., "Chimeric reverse transcriptase of Moloney murine leukaemia virus, having the YXDD box of a *Drosophila* retrotransposon, 17.6," *Biochimica et Biophysica Acta 1163*:223-226, Elsevier Science Publishers B.V. (1993).

Kati, W.M., et al., "Mechanism and Fidelity of HIV Reverse Transcriptase," *J. Biol. Chem. 267*:25988-25997, American Society for Biochemistry and Molecular Biology (1992).

Kaushik, N., et al., "Tyrosine 222, a Member of the YXDD Motif of MuLv RT, Is Catalytically Essential and Is a Major Component of the Fidelity Center," *Biochemistry 38*:2617-2627, The American Chemical Society (Mar. 1999; published on the web Feb. 10, 1999).

Kaushik, N., et al., "Role of Glutamine-151 of Human Immunodeficiency Virus Type-1 Reverse Transcriptase in RNA-Directed DNA Synthesis," *Biochemistry 36*:14430-14438, The American Chemical Society (1997).

Kaushik, N., et al., "Role of Glutamine 151 of Human Immunodeficiency Virus Type-1 Reverse Transcriptase in Substrate Selection As Assessed by Site-Directed Mutagensis," *Biochemistry 39*:2912-2920, The American Chemical Society (Mar. 2000; published on the web Feb. 22, 2000).

Kerr, S.G., and Anderson, K.S., "RNA Dependent DNA Replication Fidelity of HIV-1 Reverse Transcriptase: Evidence of Discrimination between DNA and RNA Substrates," *Biochemistry 36*:14056-14063, The American Chemical Society (1997).

Kew, Y., et al., "The Nucleoside Analog-Resistant E89G Mutant of Human Immunodeficiency Virus Type 1 Reverse Transcriptase Displays a Broader Cross-Resistance That Extends to Nonnucleoside Inhibitors," *Antimicrobial Agents and Chemotherapy 40*:1711-1714, The American Society for Microbiology (1996).

Kim, B., et al., "New Human Immunodeficiency Virus, Type 1 Reverse Transcriptase (HIV-1 RT) Mutants with Increased Fidelity of DNA Synthesis," *J. Biol. Chem.* 274:27666-27673, American Society for Biochemistry and Molecular Biology (Sep. 1999).

Kim, B., et al., "Human Immunodeficiency Virus Reverse Transcriptase," *J. Biol. Chem.* 271:4872-4878, American Society for Biochemistry and Molecular Biology (1996).

Kim, B., "Genetic Selection in *Escherichia coli* for Active Human Immunodeficiency Virus Reverse Transcriptase Mutants," *Methods* 12:318-324, Academic Press (1997).

Kim, B., et al., "Fidelity of Mutant HIV-1 Reverse Transcriptases: Interaction with the Single-Stranded Template Influences the Accuracy of DNA Synthesis," *Biochemistry* 37:5831-5839, The American Chemical Society (1998).

Larder, B.A., et al., "Site-specific mutagenesis of AIDS virus reverse transcriptase," *Nature* 327:716-717, Macmillan Magazines Ltd (1987).

Mao, J-R., et al., "An Unusual Bacterial Reverse Transcriptase Having LVDD in the YXDD Box from *Escherichia coli*," *Biochem. Biophys. Res. Comm.* 227:489-493, Academic Press (1996).

Martin-Hernandez, A.M., et al., "Human immunodeficiency virus type 1 reverse transcriptase: role of Tyr115 in deoxynucleotide binding and misinsertion fidelity of DNA synthesis," *EMBO J.* 15:4434-4442, Oxford University Press (1996).

Martin-Hernandez, A.M., et al., "Mispair extension fidelity of human immunodeficiency virus type 1 reverse transcriptases with amino acid substitutions affecting Tyr115," *Nucleic Acids Res.* 25:1383-1389, Oxford University Press (1997).

Dude Essink, B.B., et al., "Increased polymerase fidelity of the 3TC-resistant variants of HIV-1 reverse transcriptase," *Nucleic Acids Res.* 25:3212-3217, Oxford University Press (1997).

Pandey, V.N., et al., "Role of Methionine 184 of Human Immunodeficiency Virus Type-1 Reverse Transcriptase in the Polymerase Function and Fidelity of DNA Synthesis," *Biochemistry* 35:2168-2179, The American Chemical Society (1996).

Patel, P.K., et al., "Insights into DNA Polymerization Mechanisms from Structure and Function Analysis of HIV-1 Reverse Transcriptase," *Biochemistry* 34:5351-5363, The American Chemical Society (1995).

Perrino, F.W., et al., "Extension of mismatched 3' termini of DNA is a major determinant of the infidelity of human immunodeficiency virus type 1 reverse transcriptase," *Proc. Natl. Acad. Sci. USA* 86:8343-8347, The National Academy of Sciences of the USA (1989).

Pop, M.P., and Biebricher, C.K., "Kinetic Analysis of Pausing and Fidelity of Human Immunodeficiency Virus Type 1 Reverse Transcription," *Biochemistry* 35:5054-5062, The American Chemical Society (1996).

Quan, Y., et al., "Endogenous Reverse Transcriptase Assays Reveal Synergy between Combinations of the M184V and other Drug Resistance-conferring Mutations in Interactions with Nucleoside Analog Triphosphates," *J. Mol. Biol.* 277:237-247, Academic Press (1998).

Quan, Y., et al., "Dominance of the E89G Substitution in HIV-1 Reverse Transcriptase in Regard to Increased Polymerase Processivity and Patterns of Pausing," *J. Biol. Chem.* 273:21918-21925, American Society for Biochemistry and Molecular Biology (1998).

Rezende, L.F., et al., "The Impact of Multidideoxynucleoside Resistance-Conferring Mutations in Human Immunodeficiency Virus Type 1 Reverse Transcripatase on Polymerase Fidelity and Error Specificity," *J. Virol.* 72:2890-2895, The American Society for Microbiology (1998).

Rezende, L.F., et al., "The influence of 3TC resistance mutation M184I on the fidelity and error specficity of human immunodeficiency virus type 1 reverse transcriptase," *Nucleic Acids Res.* 26:3066-3072, Oxford University Press (1998).

Roberts, J.D., et al., "The Accuracy of Reverse Transcriptase from HIV-1," *Science* 242:1171-1173, American Association for the Advancement of Science (1988).

Rubinek, T., et al., "The fidelity of 3' misinsertion and mispair extensiion during DNA synthesis exhibited by two drug-resistant mutants of the reverse transcriptase of human immunodeficiency virus type 1 with Leu74→Val and Glu89→Gly," *Eur. J. Biochem.* 247:238-247, Springer International (1997).

Sarafinanos, S.G., et al., "Glutamine 151 Participates in the Substrate dNTP Binding Function of HIV-1 Reverse Transcriptase," *Biochemistry* 34:7207-7216, The American Chemical Society (1995).

Sarafianos, S.G., et al., "Site-directed Mutagenesis of Arginine 72 of HIV-1 Reverse Transcriptase," *J. Biol. Chem.* 270:19729-19735, American Society for Biochemistry and Molecular Biology (1995).

Schultz, S.J., et al., "Polypurine Tract Primer Generation and Utilization by Moloney Murine Leukemia Virus Reverse Transcriptase," *J. Biol. Chem.* 274:34547-34555, American Society for Biocehlmistry and Molecular Biology (Dec. 1999).

Song, Q., et al., "Mutagenesis of the Glu-89 Residue in Human Immunodeficiency Virus Type 1 (HIV-1) and HIV-2 Reverse Transcriptases: Effects on Nucleoside Analog Resistance," *J. Virol.* 66:7568-7571, The American Society for Microbiology (1992).

Sooknanan, R., et al., "Fidelity of Nucleic Acid Amplification with Avian Myeloblastosis Virus Reverse Transcriptase and T7 RNA Polymerase," *BioTechniques* 17:1077-1082, Eaton Publishing Co (1994).

Taube, R., et al., "The fidelity of misinsertion and mispair extension throughout DNA synthesis exhibited by mutants of the reverse transcriptase of human immunodeficiency virus type 2 resistant to nucleoside analogs," *Eur. J. Biochem.* 250:106-114, Springer International (1997).

Varela-Echavarria, A., et al., "Comparison of Moloney Murine Leukemia Virus Mutation Rate with the Fidelity of Its Reverse Transcriptase *in Vitro*," *J. Biol. Chem.* 267:24681-24688, American Society for Biochemistry and Molecular Biology (1992).

Wainberg, M.A., et al., "Enhanced Fidelity of 3TC-Selected Mutant HIV-1 Reverse Transcriptase," *Science* 271:1282-1285, American Association for the Advancement of Science (1996).

Wakefield, J.K., et al., "In Vitro Enzymatic Activity of Human Immunodifficiency Virus Type 1 Reverse Transcriptase Mutants in the Highly Conserved YMDD Amino Acid Motif Correlates with the Infectious Potential of the Proviral Genome," *J. Virol.* 66:6806-6812, The American Society for Microbiology (1992).

Weber, J., and Grosse, F., "Fidelity of human immunodeficiency virus type I reverse transcriptase in copying natural DNA," *Nucleic Acids Res.* 17:1379-1393, Oxford University Press (1989).

Wilson, J.E., et al., "Human Immunodeficiency Virus Type-1 Reverse Transcriptase," *J. Biol. Chem.* 271:13656-13662, American Society for Biochemistry and Molecular Biology (1996).

Wöhrl, B.M., et al., "Footprint Analysis of Replicating Murine Leukemia Virus Reverse Transcriptase," *Science* 267:96-99, American Association for the Advancement of Science (1995).

Yadav, P.N.S., et al., "A Computer-assisted Analysis of Conserved Residues in the Three-dimensional Structures of the Polymerase Domains of *Escherichia coli* DNA Polymerase I and HIV-1 Reverse Transcriptase," *J. Biol. Chem.* 269:716-720, American Society for Biochemistry and Molecular Biology (1994).

Yu, H., and Goodman, M.F., "Comparison of HIV-1 and Avian Myeloblastosis Virus Reverse Transcriptase Fidelity on RNA and DNA Templates," *J. Biol. Chem.* 267:10888-10896, American Society for Biochemistry and Molecular Biology (1992).

Co-pending U.S. Appl. No. 60/189;454, filed Mar. 15, 2000.
Co-pending U.S. Appl. No. 09/677,574, filed Oct. 3, 2000.
Co-pending U.S. Appl. No. 09/845,157, filed May 1, 2001.
Co-pending U.S. Patent Application filed Jul. 12, 2001, Application No. to be assigned.

Lewis, D.A. et al., "Uniquely Altered DNA Replication Fidelity Conferred by an Amino Acid Change in the Nucleotide Binding Pocket of Human Immunodeficiency Virus Type 1 Reverse Transcriptase," *J. Biol. Chem.* 274:32924-32930, American Society for Biochemistry and Molecular Biology, Inc. (Nov. 1999).

Ding, J., et al., "Structure and Functional Implications of the Polymerase Active Site Region in a Complex of HIV-1 RT with a Double-stranded DNA Template-primer and an Antibody Fab Fragment at 2.8 Å Resolution," *J. Mol. Biol.* 284:1095-1111, Academic Press, Inc. (Dec. 1998).

Harrison, G.P., et al., "Pausing of reverse transcriptase on retroviral RNA templates is influenced by secondary structures both 5' and 3' of the catalytic site," *Nucl. Acids Res.* 26:3433-3442, Oxford University Press (Jul. 1998).

Huang, H., et al., "Structure of a Covalently Trapped Catalytic Complex of HIV-1 Reverse Transcriptase: Implications for Drug Resistance," *Science* 282:1669-1675, American Association for the Advancement of Science (1998).

Jacobo-Molina, A., et al., "Crystal structure of human immunodeficiency virus type 1 reverse transcriptase complexed with double-stranded DNA at 3.0 Å resolution shows bent DNA," *Proc. Natl. Acad. Sci. USA* 90:6320-6324, National Academy of Sciences of the USA (1993).

Kohlstaedt, L.A., et al., "Crystal Structure at 3.5 Å Resolution of HIV-1 Reverse Transcriptase Complexed with an Inhibitor," *Science* 256:1783-1790, American Association for the Advancement of Science (1992).

Dialog File 351, Accession No. 13254030, unverified English language abstract of JP 2000-139457 (Document AN1).

Kaushik, N., et al., "Valine of the YVDD Motif of Moloney Murine Leukemia Virus Reverse Transcriptase: Role in the Fidelity of DNA Synthesis," *Biochemistry* 39:5155-5165, American Chemical Society (2000), published on the Web Apr. 7, 2000.

Matathias, A., et al., "SuperScript™ II RNase H Reverse Transcriptase" FocusOn Technical Bulletin 18064-3 [online], 1999 [retrieved on Feb. 2, 2006]. Retrieved fromt the Internet: <URL: http://www.lifetech.com> (10 pages).

Halvas, E.K., et al., "Development of an In Vivo Assay To Identify Structural Determinants in Murine Leukemia Virus Reverse Transcriptase Important for Fidelity," *J. Virol.* 74:312-319, American Society for Microbiology (Jan. 2000).

Blain, S.W. and Goff, S.P., "Nuclease Activities of Moloney Murine Leukemia Virus Reverse Transcriptase," *J. Biol. Chem.* 268:23585-23592, The American Society for Biochemistry and Molecular Biology, Inc. (1993).

Gerard, G.F., et al., "Reverse Transcriptae. The Use of Cloned Moloney Murine Leukemia Virus Reverse Transcriptase to Synthesize DNA from RNA," *Mol. Biotechnol.* 8:61-77, Humana Press (1997).

Lawyer, F.C., et al., "Isolation, Characterization, and Expression in *Escherichia coli* of the DNA Polymerase Gene from *Thermus aquaticus*," *J. Biol. Chem.* 264:6427-6437, The American Society for Biochemistry and Molecular Biology, Inc. (1989).

Stratagene, "Gene Characterization Kits," Stratagene Catalog, Stratagene, p. 39 (1988).

Copy of Office Action for U.S. Appl. No. 09/845,157, Smith et al., filed May 1, 2001, dated Jul. 12, 2002.
Copy of Office Action for U.S. Appl. No. 09/845,157, Smith et al., filed May 1, 2001, dated Sep. 16, 2002.
Copy of Office Action for U.S. Appl. No. 09/845,157, Smith et al., filed May 1, 2001, dated Feb. 6, 2003.
Copy of Office Action for U.S. Appl. No. 09/845,157, Smith et al., filed May 1, 2001, dated Jul. 28, 2003.
Copy of Office Action for U.S. Appl. No. 09/845,157, Smith et al., filed May 1, 2001, dated Sep. 29, 2003.
Copy of Office Action for U.S. Appl. No. 09/845,157, Smith et al., filed May 1, 2001, dated May 10, 2004.
Copy of Office Action for U.S. Appl. No. 09/845,157. Smith et al., filed May 1, 2001, dated Jun. 15, 2004.
Copy of Office Action for U.S. Appl. No. 09/845,157, Smith et al., filed May 1, 2001, dated Nov. 4, 2004.

* cited by examiner

```
0  1                                                                    1078
ATG ACC CTA AAT ATA GAA GAT GAG CAT CGG CTA CAT GAG ACC TCA AAA GAG CCA GAT GTT
MET Thr Leu Asn Ile Glu Asp Glu His Arg Leu His Glu Thr Ser Lys Glu Pro Asp Val

1138
TCT CTA GGG TCC ACA TGG CTG TCT GAT TTT CCT CAG GCC TGG GCG GAA ACC GGG GGC ATG
Ser Leu Gly Ser Thr Trp Leu Ser Asp Phe Pro Gln Ala Trp Ala Glu Thr Gly Gly MET

1198
GGA CTG GCA GTT CGC CAA GCT CCT CTG ATC ATA CCT CTG AAA GCA ACC TCT ACC CCC GTG
Gly Leu Ala Val Arg Gln Ala Pro Leu Ile Ile Pro Leu Lys Ala Thr Ser Thr Pro Val

1258
TCC ATA AAA CAA TAC CCC ATG TCA CAA GAA GCC AGA CTG GGG ATC AAG CCC CAC ATA CAG
Ser Ile Lys Gln Tyr Pro MET Ser Gln Glu Ala Arg Leu Gly Ile Lys Pro His Ile Gln

1318
AGA CTG TTG GAC CAG GGA ATA CTG GTA CCC TGC CAG TCC CCC TGG AAC ACG CCC CTG CTA
Arg Leu Leu Asp Gln Gly Ile Leu Val Pro Cys Gln Ser Pro Trp Asn Thr Pro Leu Leu

1378
CCC GTT AAG AAA CCA GGG ACT AAT GAT TAT AGG CCT GTC CAG GAT CTG AGA GAA GTC AAC
Pro Val Lys Lys Pro Gly Thr Asn Asp Tyr Arg Pro Val Gln Asp Leu Arg Glu Val Asn

1438
AAG CGG GTG GAA GAC ATC CAC CCC ACC GTG CCC AAC CCT TAC AAC CTC TTG AGC GGG CTC
Lys Arg Val Glu Asp Ile His Pro Thr Val Pro Asn Pro Tyr Asn Leu Leu Ser Gly Leu

1498
CCA CCG TCC CAC CAG TGG TAC ACT GTG CTT GAT TTA AAG GAT GCC TTT TTC TGC CTG AGA
Pro Pro Ser His Gln Trp Tyr Thr Val Leu Asp Leu Lys Asp Ala Phe Phe Cys Leu Arg
```

FIG. 8A

```
                                                                                1558
CTC CAC CCC ACC AGT CAG CCT CTC TTC GCC TTT GAG TGG AGA GAT CCA GAG ATG GGA ATC
Leu His Pro Thr Ser Gln Pro Leu Phe Ala Phe Glu Trp Arg Asp Pro Glu MET Gly Ile

1618
TCA GGA CAA TTG ACC TGG ACC AGA CTC CCA CAG GGT TTC AAA AAC AGT CCC ACC CTG TTT
Ser Gly Gln Leu Thr Trp Thr Arg Leu Pro Gln Gly Phe Lys Asn Ser Pro Thr Leu Phe

1678
GAT GAG GCA CTG CAC AGA GAC CTA GCA GAC TTC CGG ATC CAG CAC CCA GAC TTG ATC CTG
Asp Glu Ala Leu His Arg Asp Leu Ala Asp Phe Arg Ile Gln His Pro Asp Leu Ile Leu

1738
CTA CAG TAC GTG GAT GAC TTA CTG CTG GCC GCC ACT TCT GAG CTA GAC TGC CAA CAA GGT
Leu Gln Tyr Val Asp Asp Leu Leu Leu Ala Ala Thr Ser Glu Leu Asp Cys Gln Gln Gly

1798
ACT CGG GCC CTG TTA CAA ACC CTA GGG AAC CTC GGG TAT CGG GCC TCG GCC AAG AAA GCC
Thr Arg Ala Leu Leu Gln Thr Leu Gly Asn Leu Gly Tyr Arg Ala Ser Ala Lys Lys Ala

1858
CAA ATT TGC CAG AAA CAG GTC AAG TAT CTG GGG TAT CTT CTA AAA GAG GGT CAG AGA TGG
Gln Ile Cys Gln Lys Gln Val Lys Tyr Leu Gly Tyr Leu Leu Lys Glu Gly Gln Arg Trp

1918
CTG ACT GAG GCC AGA AAA GAG ACT GTG ATG GGG CAG CCT ACT CCG AAG ACC CCT CGA CAA
Leu Thr Glu Ala Arg Lys Glu Thr Val MET Gly Gln Pro Thr Pro Lys Thr Pro Arg Gln

1978
CTA AGG GAG TTC CTA GGG ACG GCA GGC TTC TGT CGC CTC TGG ATC CCT GGG TTT GCA GAA
Leu Arg Glu Phe Leu Gly Thr Ala Gly Phe Cys Arg Leu Trp Ile Pro Gly Phe Ala Glu

2038
ATG GCA GCC CCC TTG TAC CCT CTC ACC AAA ACG GGG ACT CTG TTT AAT TGG GGC CCA GAC
MET Ala Ala Pro Leu Tyr Pro Leu Thr Lys Thr Gly Thr Leu Phe Asn Trp Gly Pro Asp
```

FIG 8B

```
                                                                    2098
CAA CAA AAG GCC TAT CAA GAA ATC AAG CAA GCT CTT CTA ACT GCC CCA GCC CTG GGG TTG
Gln Gln Lys Ala Tyr Gln Glu Ile Lys Gln Ala Leu Leu Thr Ala Pro Ala Leu Gly Leu

2158
CCA GAT TTG ACT AAG CCC TTT GAA CTC TTT GTC GAC GAG AAG CAG GGC TAC GCC AAA GGT
Pro Asp Leu Thr Lys Pro Phe Glu Leu Phe Val Asp Glu Lys Gln Gly Tyr Ala Lys Gly

2218
GTC CTA ACG CAA AAA CTG GGA CCT TGG CGT CGG CCG GTG GCC TAC CTG TCC AAA AAG CTA
Val Leu Thr Gln Lys Leu Gly Pro Trp Arg Arg Pro Val Ala Tyr Leu Ser Lys Lys Leu

2278
GAC CCA GTA GCA GCT GGG TGG CCC CCT TGC CTA CGG ATG GTA GCA GCC ATT GCC GTA CTG
Asp Pro Val Ala Ala Gly Trp Pro Pro Cys Leu Arg MET Val Ala Ala Ile Ala Val Leu

2338
ACA AAG GAT GCA GGC AAG CTA ACC ATG GGA CAG CCA CTA GTC ATT CTG GCC CCC CAT GCA
Thr Lys Asp Ala Gly Lys Leu Thr MET Gly Gln Pro Leu Val Ile Leu Ala Pro His Ala

2398
GTA GAG GCA CTA GTC AAA CAA CCC CCC GAC CGC TGG CTT TCC AAC GCC CGG ATG ACT CAC
Val Glu Ala Leu Val Lys Gln Pro Pro Asp Arg Trp Leu Ser Asn Ala Arg MET Thr His

2458
TAT CAG GCC TTG CTT TTG GAC ACG GAC CGG GTC CAG TTC GGA CCG GTG GTA GCC CTG AAC
Tyr Gln Ala Leu Leu Leu Asp Thr Asp Arg Val Gln Phe Gly Pro Val Val Ala Leu Asn

2518
CCG GCT ACG CTG CTC CCA CTG CCT GAG GAA GGG CTG CAA CAC AAC TGC CTT GAT AAT TCC
Pro Ala Thr Leu Leu Pro Leu Pro Glu Glu Gly Leu Gln His Asn Cys Leu Asp Asn Ser

2533
CGC TTA ATT AAT TAA
Arg Leu Ile Asn
```

FIG 8C

SEQUENCE LISTING

<160> NUMBER OF SEQ ID NOS: 4

<210> SEQ ID NO 1
<211> LENGTH: 47
<212> TYPE: DNA
<213> ORGANISM: Artificial Sequence
<220> FEATURE:
<223> OTHER INFORMATION: Synthetic oligonucleotide template

<400> SEQUENCE: 1
gagttacagt gtttttgttc cagtctgtag cagtgtgtga atggaag                47

-continued

```
<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 2
cttccattca cacactgc                                              18

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 3
gaagatcgca ctccagccag c                                          21

<210> SEQ ID NO 4
<211> LENGTH: 298
<212> TYPE: DNA
<213> ORGANISM: Artificial Sequence
<220> FEATURE:
<223> OTHER INFORMATION: lacZa peptide in M13mp19 from SuperScript II RT
      and SuperScript II H203R T306K F309N

<400> SEQUENCE: 4
agcgcaacgc aattaatgtg agttagctca ctcattaggc accccaggct ttacacttta    60
tgcttccggc tcgtatgttg tgtggaattg tgagcggata acaatttcac acaggaaaca   120
gctatgacca tgattacgcc aagcttgcat gcctgcaggt cgactctaga ggatccccgg   180
gtaccgagct cgaattcact ggccgtcgtt ttacaacgtc gtgactggga aaaccctggc   240
gttacccaac ttaatcgcct tgcagcacat cccccttttcg ccagctggcg taatagcg    298
```

HIGH FIDELITY REVERSE TRANSCRIPTASES AND USES THEREOF

CROSS REFERENCE TO RELATED APPLICATIONS

The present application claims the benefit of U.S. Provisional Application No. 60/189,454, filed Mar. 15, 2000, the contents of which are incorporated by reference herein in their entirety.

FIELD OF THE INVENTION

The present invention is in the fields of molecular and cellular biology. The invention is generally related to reverse transcriptase enzymes and methods for the reverse transcription of nucleic acid molecules, especially messenger RNA molecules. Specifically, the invention relates to reverse transcriptase enzymes which have been mutated or modified to increase fidelity, and/or decrease terminal deoxynucleotidyl transferase activity, and to methods of producing, amplifying or sequencing nucleic acid molecules (particularly cDNA molecules) using these reverse transcriptase enzymes or compositions. The invention also relates to nucleic acid molecules produced by these methods and to the use of such nucleic acid molecules to produce desired polypeptides. The invention also concerns kits comprising such enzymes or compositions.

BACKGROUND OF THE INVENTION cDNA and cDNA Libraries

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene encodes. In order to produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist a myriad of mRNA species, each encoding a separate and specific protein. This fact provides a powerful tool to investigators interested in studying genetic expression in a tissue or cell—mRNA molecules may be isolated and further manipulated by various molecular biological techniques, thereby allowing the elucidation of the full functional genetic content of a cell, tissue or organism.

One common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or agarose, to which oligomers of thymidine (T) have been complexed. Since the 3' termini on most eukaryotic mRNA molecules contain a string of adenosine (A) bases, and since A binds to T, the mRNA molecules can be rapidly purified from other molecules and substances in the tissue or cell extract. From these purified mRNA molecules, cDNA copies may be made using the enzyme reverse transcriptase (RT), which results in the production of single-stranded cDNA molecules. The single-stranded cDNAs may then be converted into a complete double-stranded DNA copy (i.e., a double-stranded cDNA) of the original mRNA (and thus of the original double-stranded DNA sequence, encoding this mRNA, contained in the genome of the organism) by the action of a DNA polymerase. The protein-specific double-stranded cDNAs can then be inserted into a plasmid or viral vector, which is then introduced into a host bacterial, yeast, animal or plant cell. The host cells are then grown in culture media, resulting in a population of host cells containing (or in many cases, expressing) the gene of interest.

This entire process, from isolation of mRNA to insertion of the cDNA into a plasmid or vector to growth of host cell populations containing the isolated gene, is termed "cDNA cloning." If cDNAs are prepared from a number of different mRNAs, the resulting set of cDNAs is called a "cDNA library," an appropriate term since the set of cDNAs represents a "population" of genes comprising the functional genetic information present in the source cell, tissue or organism. Genotypic analysis of these cDNA libraries can yield much information on the structure and function of the organisms from which they were derived.

Retroviral Reverse Transcriptase Enzymes

Three prototypical forms of retroviral RT have been studied thoroughly. Moloney Murine Leukemia Virus (M-MLV) RT contains a single subunit of 78 kDa with RNA-dependent DNA polymerase and RNase H activity. This enzyme has been cloned and expressed in a fully active form in *E. coli* (reviewed in Prasad, V. R., *Reverse Transcriptase*, Cold Spring Harbor, N.Y.: Cold Spring Harbor Laboratory Press, p. 135 (1993)). Human Immunodeficiency Virus (HIV) RT is a heterodimer of p66 and p51 subunits in which the smaller subunit is derived from the larger by proteolytic cleavage. The p66 subunit has both a RNA-dependent DNA polymerase and an RNase H domain, while the p51 subunit has only a DNA polymerase domain. Active HIV p66/p51 RT has been cloned and expressed successfully in a number of expression hosts, including *E. coli* (reviewed in Le Grice, S. F. J., *Reverse Transcriptase*, Cold Spring Harbor, N.Y.: Cold Spring Harbor Laboratory press, p. 163 (1993)). Within the HIV p66/p51 heterodimer, the 51-kD subunit is catalytically inactive, and the 66-kD subunit has both DNA polymerase and RNase H activity (Le Grice, S. F. J., et al., *EMBO Journal* 10:3905 (1991); Hostomsky, Z., et al., *J. Virol.* 66:3179 (1992)). Avian Sarcoma-Leukosis Virus (ASLV) RT, which includes but is not limited to Rous Sarcoma Virus (RSV) RT, Avian Myeloblastosis Virus (AMV) RT, Avian Erythroblastosis Virus (AEV) Helper Virus MCAV RT, Avian Myelocytomatosis Virus MC29 Helper Virus MCAV RT, Avian Reticuloendotheliosis Virus (REV-T) Helper Virus REV-A RT, Avian Sarcoma Virus UR2 Helper Virus UR2AV RT, Avian Sarcoma Virus Y73 Helper Virus YAV RT, Rous Associated Virus (RAV) RT, and Myeloblastosis Associated Virus (MAV) RT, is also a heterodimer of two subunits, α (approximately 62 kDa) and β (approximately 94 kDa), in which α is derived from β by proteolytic cleavage (reviewed in Prasad, V. R., *Reverse Transcriptase*, Cold Spring Harbor, N.Y.: Cold Spring Harbor Laboratory Press (1993), p. 135). ASLV RT can exist in two additional catalytically active structural forms, ββ and α (Hizi, A. and Joklik, W. K., *J. Biol. Chem.* 252: 2281 (1977)). Sedimentation analysis suggests αβ and ββ are dimers and that the α form exists in an equilibrium between monomeric and dimeric forms (Grandgenett, D. P., et al., *Proc. Nat. Acad. Sci. USA* 70: 230 (1973); Hizi, A. and Joklik, W. K., *J. Biol. Chem.* 252: 2281 (1977); and Soltis, D. A. and Skalka, A. M., *Proc. Nat. Acad. Sci. USA* 85: 3372 (1988)). The ASLV αβ and ββ RTs are the only known examples of retroviral RT that include three different activities in the same protein complex: DNA polymerase, RNase H, and DNA endonuclease (integrase) activities (reviewed in Skalka, A. M., *Reverse Transcriptase*, Cold Spring Harbor, N.Y.: Cold Spring Harbor Laboratory Press (1993), p. 193). The α form lacks the integrase domain and activity.

Various forms of the individual subunits of ASLV RT have been cloned and expressed. These include a 98-kDa precursor polypeptide that is normally processed proteolytically to β and a 4-kDa polypeptide removed from the β carboxy end (Alexander, F., et al., *J. Virol.* 61: 534 (1987) and Anderson, D. et al., *Focus* 17:53 (1995)), and the mature β subunit (Weis, J. H. and Salstrom, J. S., U.S. Pat. No. 4,663,290 (1987); and Soltis, D. A. and Skalka, A. M., *Proc. Nat. Acad. Sci. USA* 85:3372 (1988)). Heterodimeric RSV αβ RT has also been purified from *E. coli* cells expressing a cloned RSV β gene (Chernov, A. P., et al., *Biomed. Sci.* 2:49 (1991)).

Various domains of the reverse transcriptases have also been identified, for example, the thumb, fingers and palm regions. The thumb region is of particular importance in that, mutations in this region have been shown to reduce the incidence of frame shifting.

Reverse Transcription Efficiency and Fidelity

As noted above, the conversion of mRNA into cDNA by RT-mediated reverse transcription is an essential step in the study of proteins expressed from cloned genes. However, the use of unmodified RT to catalyze reverse transcription is inefficient for at least two reasons. First, RT sometimes renders an RNA template unable to be copied before reverse transcription is initiated or completed, primarily due to the intrinsic RNase H activity present in RT. Second, RTs generally have low fidelity. That is, RTs incorporate mismatched bases during cDNA synthesis thus producing cDNA products having sequence errors. RTs have in fact been shown to incorporate one base error per 3000–6000 nucleotides for HIV RT, and 1/10,000 nucleotide for AMV RT during cDNA synthesis (Berger, S. L., et al., *Biochemistry* 22:2365–2372 (1983); Krug, M. S., and Berger, S. L., *Meth. Enzymol.* 152:316 (1987); Berger et al. *Meth. Enzymol.* 275: 523 (1996)).

Removal of the RNase H activity of RT can eliminate the first problem and improve the efficiency of reverse transcription (Gerard, G. F., et al., *FOCUS* 11(4):60 (1989); Gerard, G. F., et al., *FOCUS* 14(3):91 (1992)). However such RTs ("RNase H⁻" forms) do not address the second problem of improving the fidelity of reverse transcription. The present invention addresses this need.

SUMMARY OF THE INVENTION

The present invention provides reverse transcriptase enzymes, compositions comprising such enzymes and methods useful in overcoming the efficiency limitations of reverse transcription. In general, the invention provides compositions for use in high fidelity reverse transcription of a nucleic acid molecule comprising one or more polypeptides having reverse transcriptase activity of the invention. Such compositions may further comprise one or more nucleotides, a suitable buffer, and/or one or more DNA polymerases. The compositions of the invention may also comprise one or more oligonucleotide primers.

The reverse transcriptases of the invention are preferably modified or mutated such that the fidelity of the enzyme is increased or enhanced. Additional embodiments of the invention include reverse transcriptases that are modified to decrease or eliminate terminal deoxynucleotidyl transferase (TdT) activity. The reverse transcriptases of the invention are preferably single chained (single-subunit) or multi-chained (multi-subunit), and are reduced or substantially reduced in RNase H activity, and most preferably are enzymes selected from the group consisting of Moloney Murine Leukemia Virus (M-MLV) H⁻ reverse transcriptase, Rous Sarcoma Virus (RSV) H⁻ reverse transcriptase, Avian Myeloblastosis Virus (AMV) H⁻ reverse transcriptase, Rous Associated Virus (RAV) H⁻ reverse transcriptase, Myeloblastosis Associated Virus (MAV) H⁻ reverse transcriptase and Human Immunodeficiency Virus (HIV) H⁻ reverse transcriptase or other ASLV H⁻ reverse transcriptases. In preferred compositions, the reverse transcriptases are present at working concentrations.

Enzymes of the invention include reverse transcriptases which exhibit reverse transcriptase activity either upon the formation of multimers (e.g., dimers) or as individual protein molecules (i.e., in monomeric form). Examples of reverse transcriptases which exhibit reverse transcriptase activity upon the formation of multimers include AMV, RSV and HIV reverse transcriptases. An example of a reverse transcriptases which exhibits reverse transcriptase activity as separate, individual proteins include M-MLV and RSV reverse transcriptase.

Multimeric reverse transcriptases of the invention may form homo-multimers or hetero-multimers. In other words, the subunits of the multimeric protein complex may be identical or different. One example of a hetero-dimeric reverse transcriptase is AMV reverse transcriptase, which is composed of two subunits that differ in primary amino acid sequence. More specifically, as already discussed, AMV reverse transcriptase may be composed of two subunits wherein one of these subunits is generated by proteolytic processing of the other. Thus, dimeric AMV reverse transcriptase may be composed of subunits of differing size that share regions of amino acid sequence identity.

The present invention relates in particular to mutant or modified reverse transcriptases wherein one or more amino acid changes have been made which renders the enzyme more faithful (higher fidelity) in nucleic acid synthesis. The preferred sites for mutation or modification to produce higher fidelity polymerases are listed for some reverse transcriptases in Table 1. Similar or equivalent sites or corresponding sites in other reverse trancriptases can be mutated to produce higher fidelity reverse transcriptases.

TABLE 1

| RT | Amino acid |
|---|---|
| M-MLV | Y64, R116, K152, Q190, T197, V223, D124, H126, Y133 |
| AMV | W25, R76, K110, Q149, T156, M182 |
| RSV | W25, R76, K110, Q149, T156, M182 |
| HIV | W24, R78, G112, Q151, A158, M184 |

The invention further includes M-MLV RT having the following mutations: V223H, Q190F, T197A, T197E, Y64W, R116M and K152R as well as other RTs having corresponding mutations or modifications.

The present invention is also directed to mutant or modified reverse transcriptases wherein one or more amino acid changes have been made which decrease or eliminate terminal deoxynucleotidyl transferase (TdT) activity. The preferred sites for these mutations include, but are not limited to, F309, T197 and Y133 of M-MLV RT. Specific mutations or modifications of M-MLV RT include T197E, which reduces TdT activity to a level undetectable by assay methods described herein; and T197A, which reduces TdT activity, to a lesser extent. Similar or equivalent sites or corresponding sites in other reverse transcriptases can be mutated to produce reverse transcriptases with reduced, substantially reduced or eliminated TdT activities. Examples of such equivalent sites include, but are not limited to, W266 and I194 in HIV RT, W267 and A95 in AMV RT, and W267 and A95 in RSV RT.

In specific embodiments, reverse transcriptases of the invention may not include M-MLV RT, HIV RT, AMV RT, or RSV RT. Thus, for example, in certain embodiments the invention includes RTs with increased fidelity that are not HIV RTs.

The present invention is also directed to DNA molecules (preferably vectors) containing a gene or nucleic acid molecule encoding the mutant or modified reverse transcriptases of the present invention and to host cells containing such DNA molecules. Any number of hosts may be used to express the gene or nucleic acid molecule of interest, including prokaryotic and eukaryotic cells. Preferably, prokaryotic cells are used to express the polymerases of the invention. The preferred prokaryotic host according to the present invention is *E. coli*.

The invention also relates to a method of producing the reverse transcriptases of the invention, said method comprising:

(a) culturing the host cell comprising a gene or nucleic acid molecule encoding a reverse transcriptase of the invention (preferably such RT gene is contained by a vector within the host cell);

(b) expressing said gene or nucleic acid molecule; and (c) isolating said reverse transcriptase from said host cell.

The invention is also directed to methods for making one or more nucleic acid molecules, comprising mixing one or more nucleic acid templates (preferably one or more RNA templates and most preferably one or more messenger RNA templates) with one or more reverse transcriptases of the invention and incubating the mixture under conditions sufficient to make a first nucleic acid molecule or molecules complementary to all or a portion of the one or more nucleic acid templates. In a preferred embodiment, the first nucleic acid molecule is a single-stranded cDNA. Nucleic acid templates suitable for reverse transcription according to this aspect of the invention include any nucleic acid molecule or population of nucleic acid molecules (preferably RNA and most preferably mRNA), particularly those derived from a cell or tissue. In a preferred aspect, a population of mRNA molecules (a number of different mRNA molecules, typically obtained from cells or tissue) are used to make a cDNA library, in accordance with the invention. Preferred cellular sources of nucleic acid templates include bacterial cells, fungal cells, plant cells and animal cells.

The invention also relates to methods for making one or more double-stranded nucleic acid molecules. Such methods comprise (a) mixing one or more nucleic acid templates (preferably RNA or mRNA, and more preferably a population of mRNA templates) with one or more reverse transcriptases of the invention; (b) incubating the mixture under conditions sufficient to make a first nucleic acid molecule or molecules complementary to all or a portion of the one or more templates; and (c) incubating the first nucleic acid molecule or molecules under conditions sufficient to make a second nucleic acid molecule or molecules complementary to all or a portion of the first nucleic acid molecule or molecules, thereby forming one or more double-stranded nucleic acid molecules comprising the first and second nucleic acid molecules. Such methods may include the use of one or more DNA polymerases as part of the process of making the one or more double-stranded nucleic acid molecules. The invention also concerns compositions useful for making such double-stranded nucleic acid molecules. Such compositions comprise one or more reverse transcriptases of the invention and optionally one or more DNA polymerases, a suitable buffer, one or more primers, and/or one or more nucleotides.

The invention also relates to methods for amplifying a nucleic acid molecule. Such amplification methods comprise mixing the double-stranded nucleic acid molecule or molecules produced as described above with one or more DNA polymerases and incubating the mixture under conditions sufficient to amplify the double-stranded nucleic acid molecule. In a first preferred embodiment, the invention concerns a method for amplifying a nucleic acid molecule, the method comprising (a) mixing one or more nucleic acid templates (preferably one or more RNA or mRNA templates and more preferably a population of mRNA templates) with one or more reverse transcriptases of the invention and with one or more DNA polymerases and (b) incubating the mixture under conditions sufficient to amplify nucleic acid molecules complementary to all or a portion of the one or more templates. Preferably, the reverse transcriptases are reduced or substantially reduced in RNase H activity and the DNA polymerases comprise a first DNA polymerase having 3' exonuclease activity and a second DNA polymerase having substantially reduced 3' exonuclease activity. The invention also concerns compositions comprising one or more reverse transcriptases of the invention and one or more DNA polymerases for use in amplification reactions. Such compositions may further comprise one or more nucleotides and/or a buffer suitable for amplification. The compositions of the invention may also comprise one or more oligonucleotide primers.

The invention is also directed to nucleic acid molecules (particularly single- or double-stranded cDNA molecules) or amplified nucleic acid molecules produced according to the above-described methods and to vectors (particularly expression vectors) comprising these nucleic acid molecules or amplified nucleic acid molecules.

The invention is also directed to recombinant host cells comprising the above-described nucleic acid molecules, amplified nucleic acid molecules or vectors. Preferred such host cells include bacterial cells, yeast cells, plant cells and animal cells (including insect cells and mammalian cells).

The invention is further directed to methods of producing a polypeptide encoded by the nucleic acid molecules produced by the methods of the invention. Such methods comprise culturing the above-described recombinant host cells and isolating the encoded polypeptide, and to a polypeptide produced by such methods.

The invention also concerns methods for sequencing one or more nucleic acid molecules using the compositions or enzymes of the invention. In specific embodiments, such methods comprise (a) mixing a nucleic acid molecule (e.g., an RNA or DNA molecules) to be sequenced with one or more primers, one or more reverse transcriptases of the invention, one or more nucleotides and one or more terminating agents, such as one or more dideoxynucleoside triphosphates; (b) incubating the mixture under conditions sufficient to synthesize a population of nucleic acid molecules complementary to all or a portion of the one or more nucleic acid molecules to be sequenced; and (c) separating members of the population of nucleic acid molecules to determine the nucleotide sequence of all or a portion of the one or more nucleic acid molecules to be sequenced.

In other embodiments, such methods comprise (a) mixing a nucleic acid molecule (e.g., an RNA or DNA molecule) to be sequenced with one or more primers, one or more reverse transcriptases of the invention, one or more nucleotides and one or more terminating agents, such as one or more dideoxynucleoside triphosphates; (b) incubating the mixture under conditions sufficient to synthesize a population of nucleic acid molecule complementary to all or a portion of the nucleic acid molecule to be sequenced; and (c) separating the population of nucleic acid molecules to determine the nucleotide sequence of all or a portion of the nucleic acid molecule to be sequenced.

The invention is also directed to kits for use in the methods of the invention. Such kits can be used for making, sequencing or amplifying nucleic acid molecules (single- or double-stranded). The kits of the invention comprise a carrier, such as a box or carton, having in close confinement therein one or more containers, such as vials, tubes, bottles and the like. In the kits of the invention, a first container contains one or more of the reverse transcriptase enzymes of the present invention. The kits of the invention may also comprise, in the same or different containers, one or more DNA polymerase (preferably thermostable DNA polymerases), one or more suitable buffers for nucleic acid synthesis and one or more nucleotides. Alternatively, the components of the kit may be divided into separate containers (e.g., one container for each enzyme and/or component). The kits of the invention also may comprise instructions or protocols for carrying out the methods of the invention. In preferred kits of the invention, the reverse transcriptases are modified or mutated such that the fidelity of cDNA synthesis is increased and/or enhanced, the reverse transcriptases are reduced or substantially reduced in RNase H activity, and are most preferably selected from the group consisting of M-MLV H⁻ reverse transcriptase, RSV H⁻ reverse transcriptase, AMV H⁻ reverse transcriptase, RAV H⁻ reverse transcriptase, MAV H⁻ reverse transcriptase and HIV H⁻ reverse transcriptase. In additional preferred kits of the invention, the enzymes (reverse transcriptases and/or DNA polymerases) in the containers are present at working concentrations.

Reverse transcriptases of the invention include any reverse transcriptase having (1) enhanced fidelity or (2) decreased or eliminated terminal deoxynucleotidyl transferase (TdT) activity. Reverse transcriptases may be single chained or multi-chained. Such reverse transcriptases include retroviral reverse transcriptases, bacterial reverse trancriptases, retrotransposon reverse trancriptases, and DNA polymerases having reverse trancriptase activity. Preferred reverse trancriptases of the invention include single-subunit reverse transcriptases (e.g., M-MLV RT) and multi-subunit reverse transcriptases (e.g., AMV RT) and preferably retroviral RTs. In particular, the invention relates to M-MLV RTs and ASLV RTs (such as AMV-RT and RSV-RT). Such reverse trancriptases of the invention preferably have reduced or substantially reduced RNAse H activity.

Other preferred embodiments of the present invention will be apparent to one of ordinary skill in light of the following drawings and description of the invention, and of the claims.

BRIEF DESCRIPTION OF THE DRAWINGS

These and other features, aspects, and advantages of the present invention will become better understood with reference to the following description and appended claims, and accompanying drawings where:

FIGS. 8A–8C. This figure depicts the DNA sequence (SEQ ID NO: 5), which encodes a wild type M-MLV reverse transcriptase having DNA polymerase activity and substantially no RNase H activity. Also shown is the corresponding amino acid sequence (SEQ ID NO: 6). Position 0 of FIG. 8A is the codon ATG, which encodes a methionine residue. The methionine residue is the initiation codon for the recombinant DNA sequence. Thus, position 0 of this sequence does not represent an amino acid residue present in the M-MLV reverse transcriptase having DNA polymerase activity and substantially no RNase H activity.

DETAILED DESCRIPTION

Figure 1:
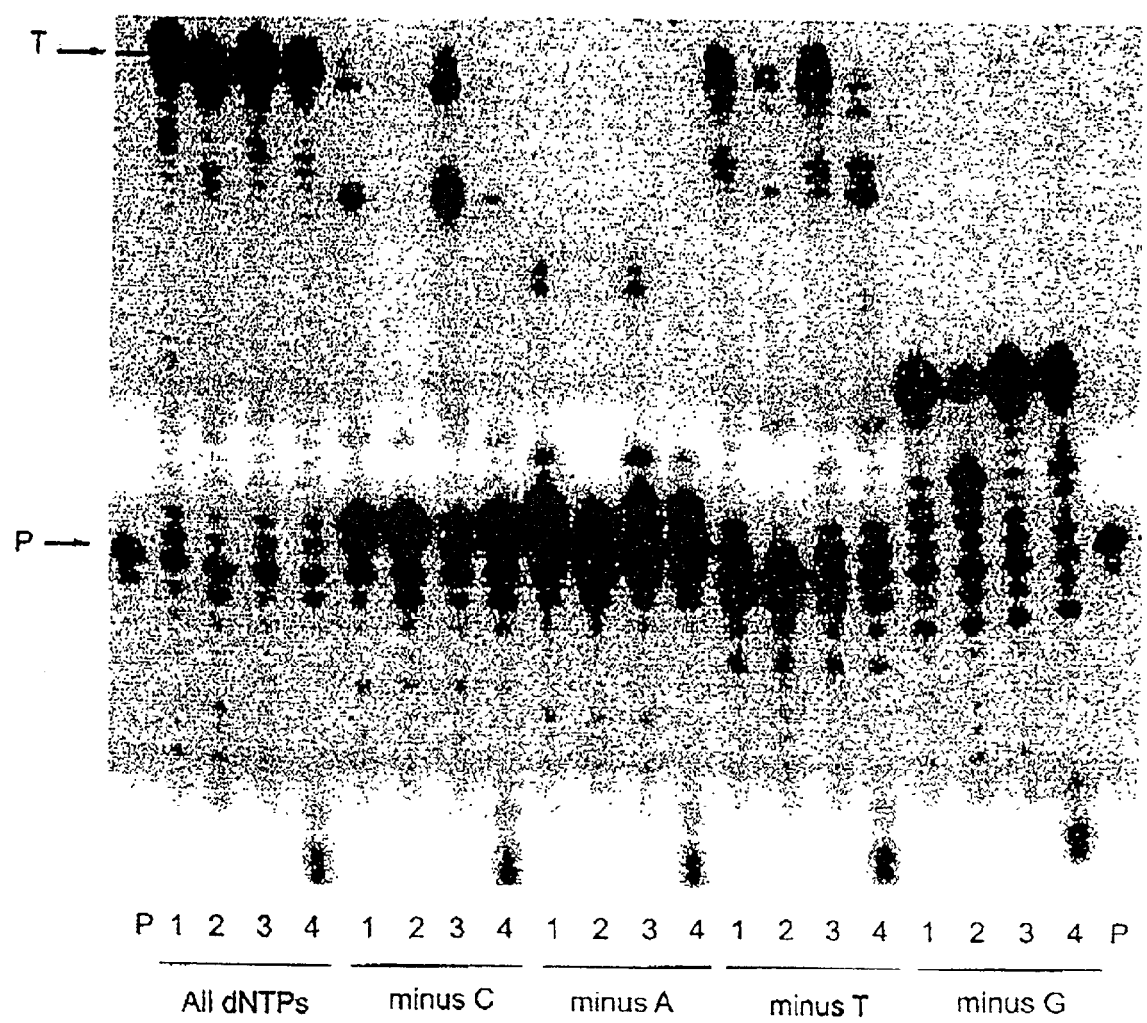
FIG. 1 represents a scanned phosphoimage, which shows misinsertion assay of SuperScript II (1) and mutant proteins V223H (2), V223F (3), and R110M (4) with DNA template. The $^{32}$P-labeled 18-mer primer annealed to a 47-mer DNA template (5 nM) was extended by equal units of RT protein at 37° C. for 30 min as seen in the extension reactions with all four nucleotides. The extension reactions were also performed in the presence of only 3 complementary dNTPs; minus dCTP, minus dATP, minus TTP, and minus dGTP. The extension reactions were analyzed by 6% denaturing gel electrophoresis. In this assay, the higher efficiency of elongation of terminated primer with only three nucleotides will reflect the lower fidelity of the M-MLV RNase H⁻ protein assayed. T, fully extended primer. P, non-extended primer.

In the description that follows, a number of terms used in recombinant DNA, virology and immunology are extensively utilized. In order to provide a clearer and consistent understanding of the specification and claims, including the scope to be given such terms, the following definitions are provided.

Cloning vector. A plasmid, cosmid or phage DNA or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are tetracycline resistance or ampicillin resistance.

Expression vector. A vector similar to a cloning vector but which is capable of enhancing the expression of a gene or nucleic acid molecules which has been cloned into it, after transformation into a host. The cloned gene or nucleic acid molecule is usually placed under the control of (i.e., operably linked to) certain control sequences such as promoter sequences.

Recombinant host. Any prokaryotic or eukaryotic microorganism which contains the desired cloned genes or nucleic acid molecule in an expression vector, cloning vector or any DNA molecule. The term "recombinant host" is also meant to include those host cells which have been genetically engineered to contain the desired gene or nucleic acid molecule on the host chromosome or genome.

Host. Any prokaryotic or eukaryotic microorganism that is the recipient of a replicable expression vector, cloning vector or any DNA molecule. The DNA molecule may contain, but is not limited to, a structural gene, a promoter and/or an origin of replication.

Promoter. A DNA sequence generally described as the 5' region of a gene, located proximal to the start codon. At the promoter region, transcription of an adjacent gene(s) is initiated.

Gene. A DNA sequence that contains information necessary for expression of a polypeptide or protein. It includes the promoter and the structural gene as well as other sequences involved in expression of the protein.

Structural gene. A DNA sequence that is transcribed into messenger RNA that is then translated into a sequence of amino acids characteristic of a specific polypeptide.

Operably linked. As used herein means that the promoter is positioned to control the initiation of expression of the polypeptide encoded by the structural gene or other nucleic acid molecule.

Expression. Expression is the process by which a gene or other nucleic acid molecule produces a polypeptide. It includes transcription of the gene or nucleic acid molecule into messenger RNA (mRNA) and the translation of such mRNA into polypeptide(s).

Substantially Pure. As used herein "substantially pure" means that the desired purified protein is essentially free from contaminating cellular contaminants which are associated with the desired protein in nature. Contaminating cellular components may include, but are not limited to, phosphatases, exonucleases, endonucleases or undesirable DNA polymerase enzymes. Prefered reverse transcriptases of the invention are substantially pure.

Primer. As used herein "primer" refers to a single-stranded oligonucleotide that is extended by covalent bonding of nucleotide monomers during amplification or polymerization of a DNA molecule.

Template. The term "template" as used herein refers to a double-stranded or single-stranded nucleic acid molecule which is to be amplified, copied or sequenced. In the case of a double-stranded DNA molecule, denaturation of its strands to form single-stranded first and second strands is performed before these molecules may be amplified, copied or sequenced. A primer, complementary to a portion of a nucleic acid template is hybridized under appropriate conditions and the reverse transcriptase of the invention may then synthesize a DNA molecule complementary to said template or a portion thereof. The newly synthesized DNA molecule, according to the invention, may be equal or shorter in length than the original template. Mismatch incorporation during the synthesis or extension of the newly synthesized DNA molecule may result in one or a number of mismatched base pairs. Thus, the synthesized DNA molecule need not be exactly complementary to the template.

Incorporating. The term "incorporating" as used herein means becoming a part of a DNA molecule or primer.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA) and deoxyribonucleotides are "incorporated" into DNA by DNA polymerases. The term nucleotide includes deoxyribonucleoside triphosphates such as dATP, dCTP, dITP, dUTP, dGTP, dTTP, or derivatives thereof. Such derivatives include, for example, [aS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Hybridization. The terms "hybridization" and "hybridizing" refer to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

Terminal extension. Terminal extension, as used herein, refers to the ability of a reverse transcriptase (RT) to add additional bases on to the 3' end of a newly synthesized cDNA strand beyond the 5' end of the mRNA template. The activity may add bases specifically (with a nucleotide bias) or randomly.

Terminal extension activity is also known as terminal deoxynucleotidyl transferase (TdT) activity. A reverse transcriptase having decreased or eliminated TdT activity is defined as any reverse transcriptase having lower TdT activity than the specific activity of the corresponding unmutated, unmodified or wild type enzyme, particularly, less than about 75% of the specific activity of the corresponding unmutated, unmodified or wild type enzyme, less than about 50% of the specific activity of the corresponding unmutated, unmodified or wild type enzyme, less than about 25% of the specific activity of the corresponding unmutated, unmodified or wild type enzyme, less than about 15% of the specific activity of the corresponding unmutated, unmodified or wild type enzyme, less than 10% of the specific activity of the corresponding unmutated, unmodified or wild type enzyme, less than about 5% of the specific activity of the corresponding unmutated, unmodified or wild type enzyme, or less than about 1% of the specific activity of the corresponding unmutated, unmodified or wild type enzyme. Eliminated TdT activity is defined as a level of activity that is undetectable by the assay methods utilized in Example 3.

Strand jumping. Strand jumping, as used herein, refers to a type of random mutation caused by an RT "skipping" more than one (e.g., two, five, ten, fifty, one-hundred, etc.) nucleotides on the mRNA template, resulting in a deletion of the corresponding nucleotides in the resulting cDNA.

Hand domain. The hand domain, as used herein, refers to those amino acids which are in the area or areas that control the template, primer, or nucleotide interaction of the reverse transcriptase. This domain is further characterized by a group of three regions of secondary structure in a reverse transcriptase enzyme, the thumb, fingers and palm regions. The thumb domain is defined as residing between amino acids 240–315 of HIV RT, or between amino acids 280–355 of M-MLV RT. The fingers domain is defined as residing between amino acids 1–85 and 120–154 of HIV RT, or between 1–124 and 161–193 of M-MLV RT. The palm domain is defined as residing between amino acids 86–199 and 155–239 of HIV RT, or between amino acids 125–160 and 193–279 of M-MLV RT. These areas are generally defined, and the amino acids defining the N-termini and C-termini are approximate. Corresponding regions can also be defined for other reverse transcriptases.

Fidelity. Fidelity refers to the accuracy of polymerization, or the ability of the reverse transcriptase to discriminate correct from incorrect substrates, (e.g., nucleotides) when synthesizing nucleic acid molecules which are complementary to a template. The higher the fidelity of a reverse transcriptase, the less the reverse transcriptase misincorporates nucleotides in the growing strand during nucleic acid synthesis; that is, an increase or enhancement in fidelity results in a more faithful reverse transcriptase having decreased error rate or decreased misincorporation rate.

A reverse transcriptase having increased/enhanced/higher fidelity is defined as a polymerase having any increase in fidelity, preferably about 1.5 to about 10,000 fold, about 2 to about 5,000 fold, or about 2 to about 2000 fold (preferably greater than about 5 fold, more preferably greater than about 10 fold, still more preferably greater than about 50 fold, still more preferably greater than about 100 fold, still more preferably greater than about 500 fold and most preferably greater than about 100 fold) reduction in the number of misincorporated nucleotides during synthesis of any given nucleic acid molecule of a given length compared to the control reverse trancriptase. Preferably, the mutant or modified RT of the invention is compared to the corresponding unmodified or wild-type RT to determine the relative enhancement or increase in fidelity. For example, a mutated reverse transcriptase may misincorporate one nucleotide in the synthesis of a nucleic acid molecule segment of 1000 bases compared to an unmutated reverse transcriptase misincorporating 10 nucleotides in the same size segment. Such a mutant reverse transcriptase would be said to have an increase of fidelity of 10 fold.

Fidelity can also be measured by the decrease in the incidence of frame shifting, as described in Example 5. A reverse transcriptase having increased fidelity is defined as a polymerase or reverse transcriptase having any increase in fidelity with respect to frame shifting, as compared to a control reverse transcriptase (e.g., a wild-type RT), for example, a reverse transcriptase having greater than about 1.5 fold increased fidelity with respect to frame shifting, having greater than about 5 fold increased fidelity with respect to frame shifting, having greater than about 10 fold increased fidelity with respect to frame shifting, having greater than about 20 fold increased fidelity with respect to frame shifting, having greater than about 30 fold increased fidelity with respect to frame shifting, or having greater than about 40 fold increased fidelity with respect to frame shifting.

A reverse transcriptase having increased/enhanced/higher fidelity, with respect to frame shifting, can also be defined as a reverse transcriptase or polymerase having any increase in fidelity, such as about 1.5 to about 10,000 fold, about 2 to about 5,000 fold, about 2 to about 2000 fold, about 1.5 to about 40 fold, about 5 to about 40 fold, about 10 to about 40 fold, about 20 to about 40 fold, about 30 to about 40 fold, about 5 to about 30 fold, about 10 to about 30 fold, about 15 to about 30 fold, about 20 to about 30 fold, about 5 to about 20 fold, about 10 to about 20 fold, about 15 to about 20 fold, about 10 to about 100 fold, about 15 to about 100 fold, about 20 to about 100 fold, about 30 to about 100 fold, or about 50 to about 100 fold.

A reverse transcriptase having reduced misincorporation is defined herein as either a mutated or modified reverse transcriptase that preferably has about or less than 50%, or preferably about or less than 25%, more preferably about or less than 10% and most preferably about or less than 1% of relative misincorporation compared to the corresponding unmutated, unmodified or wild type enzyme.

The fidelity or misincorporation rate of a reverse transcriptase can be determined by sequencing or by other methods known in the art (Eckert & Kunkel, 1990, *Nuc. Acids Res.*, 3739–3744). In one example, the sequence of a DNA molecule synthesized by the unmutated and mutated reverse transcriptase can be compared to the expected (known) sequence. In this way, the number of errors (misincorporation or frame shifts) can be determined for each enzyme and compared. In another example, the unmutated and mutated reverse transcriptase may be used to sequence a DNA molecule having a known sequence. The number of sequencing errors (misincorporation or frame shifts) can be compared to determine the fidelity or misincorporation rate of the enzymes. Other means of determining the fidelity or misincorporation rate include a forward complementation assay using an RNA template as described below and previously in Boyer J. C. et al. *Methods Enzymol.* 275: 523 (1996), and are set out in the examples. Other methods of determining the fidelity or misincorporation rate will be recognized by one of skill in the art.

In general, the invention provides compositions for use in reverse transcription of a nucleic acid molecule comprising a reverse transcriptase with one or more mutations or modifications which render the reverse transcriptase more efficient, that is having higher fidelity. The invention also provides compositions for use in reverse transcription of a nucleic acid molecule comprising a reverse transcriptase with one or more mutations or modifications which decrease TdT activity.

The enzymes in these compositions are preferably present in working concentrations and are reduced or substantially reduced in RNase H activity. Alternatively, the reverse transcriptases used in the compositions of the invention may have RNase H activity. Preferred mutated or modified reverse transcriptases are derived from M-MLV reverse transcriptase, HIV reverse transcriptase, RSV reverse transcriptase, AMV reverse transcriptase, RAV reverse transcriptase, and MAV reverse transcriptase or other ASLV reverse transcriptases or their corresponding RNase H⁻ derivatives.

In accordance with the invention, any number of mutations can be made to the RTs and in a preferred aspect, multiple mutations can be made to result in an additive fidelity increase. Such mutations include point mutations, frame shift mutations, deletions and insertions, with one or more point mutations preferred. Preferably, oligonucleotide directed mutagenesis is used to create the mutant polymerases which allows for all possible classes of base pair changes at any determined site along the encoding DNA molecule. In general, this technique involves annealing an oligonucleotide complementary (except for one or more mismatches) to a single stranded nucleotide sequence coding for the RT of interest. The mismatched oligonucleotide is then extended by DNA polymerase, generating a double-stranded DNA molecule which contains the desired change in sequence in one strand. The changes in sequence can of course result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can of course be carried out via PCR.

The invention is also directed to methods for reverse transcription of one or more nucleic acid molecules comprising mixing one or more nucleic acid templates, which is preferably RNA or messenger RNA (mRNA) and more preferably a population of mRNA molecules, with a mutant reverse transcriptase of the present invention and incubating the mixture under conditions sufficient to make a nucleic acid molecule or molecules complementary to all or a portion of the one or more templates. To make the nucleic acid molecule or molecules complementary to the one or more templates, a primer (e.g., an oligo(dT) primer) and one or more nucleotides are used for nucleic acid synthesis in the 3' to 5' direction. Nucleic acid molecules suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant or an animal (e.g, human, cow, pig, mouse, sheep, horse, monkey, canine, feline, rat, rabbit, bird, fish, insect, etc.). Such nucleic acid molecules may also be isolated from viruses.

The invention further provides methods for amplifying or sequencing a nucleic acid molecule comprising contacting the nucleic acid molecule with a reverse transcriptase of the present invention. Preferred such methods comprise one or more polymerase chain reactions (PCRs).

Sources of Reverse Transcriptases

Enzymes for use in the compositions, methods and kits of the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., *Science* 239:487–491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., commonly owned U.S. Pat. Nos. 5,948,614 and 6,015,668, which are incorporated by reference herein in their entireties). Preferred reverse transcriptases for use in the invention include M-MLV RT, AMV RT, RSV RT, RAV RT, MAV RT and generally ASLV reverse transcriptases. As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases of the invention. Fragments of reverse transcriptases may be obtained by deletion mutation by recombinant techniques that are routine and well-known in the art, or by enzymatic digestion of the reverse transcriptase(s) of interest using any of a number of well-known proteolytic enzymes.

Preferred enzymes for use in the invention include those that are reduced or substantially reduced in RNase H activity. Such enzymes that are reduced or substantially reduced in RNase H activity may be obtained by mutating the RNase H domain within the reverse transcriptase of interest, preferably by one or more point mutations, one or more deletion mutations, and/or one or more insertion mutations as described above. By an enzyme "substantially reduced in RNase H activity" is meant that the enzyme has less than about 30%, less than about 25%, 20%, more preferably less than about 15%, less than about 10%, less than about 7.5%, or less than about 5%, and most preferably less than about 5% or less than about 2%, or which lacks the RNase H activity of the corresponding wildtype or RNase H⁺ enzyme such as wildtype Moloney Murine Leukemia Virus (M-MLV), Avian Myeloblastosis Virus (AMV) or Rous Sarcoma Virus (RSV) reverse transcriptases. RTs having reduced or substantially reduced RNase H activity have been previously described (see U.S. Pat. Nos. 5,244,797; 5,405,776; 5,668,005 and 6,063,608; and WO 98/47912). The RNase H activity of any enzyme may be determined by a variety of assays, such as those described, for example, in U.S. Pat. Nos. 5,244,797; 5,405,776; 5,668,005 and 6,063,608; in Kotewicz, M. L., et al., *Nucl. Acids Res.* 16:265

(1988); and in Gerard, G. F., et al., *FOCUS* 14(5):91 (1992), the disclosures of all of which are fully incorporated herein by reference.

Particularly preferred mutated or modified enzymes for use in the invention include, but are not limited to, M-MLV H⁻ reverse transcriptase, RSV H⁻ reverse transcriptase, AMV H⁻ reverse transcriptase, RAV H⁻ reverse transcriptase, MAV H⁻ reverse transcriptase and HIV H⁻ reverse transcriptase. It will be understood by one of ordinary skill, however, that any enzyme capable of producing a DNA molecule from a ribonucleic acid molecule (i.e., having reverse transcriptase activity) that is reduced or substantially reduced in RNase H activity may be equivalently used in the compositions, methods and kits of the invention.

Polypeptides having reverse transcriptase activity for use in the invention may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, the polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372–3376 (1988)).

In a preferred aspect of the invention, mutant or modified reverse transcriptases are made by recombinant techniques. A number of cloned reverse transcriptase genes are available or may be obtained using standard recombinant techniques (see U.S. Pat. Nos. 5,244,797; 5,405,776; 5,668,005 and 6,063,608 and WO 98/47912).

To clone a gene encoding a reverse transcriptase which will be modified in accordance with the invention, isolated DNA which contains the reverse transcriptase gene is used to construct a recombinant DNA library in a vector. Any vector, well known in the art, can be used to clone the reverse transcriptase of interest. However, the vector used must be compatible with the host in which the recombinant DNA library will be transformed.

Prokaryotic vectors for constructing the plasmid library include plasmids such as those capable of replication in *E. coli* such as, for example, pBR322, ColE1, pSC101, pUC-vectors (pUC18, pUC19, etc.: In: *Molecular Cloning, A Laboratory Manual,* Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). *Bacillus* plasmids include pC194, pC221, pC217, etc. Such plasmids are disclosed by Glyczan, T. In: *The Molecular Biology Bacilli,* Academic Press, York (1982), 307–329. Suitable *Streptomyces* plasmids include pIJ101 (Kendall et al., *J. Bacteriol* 169:4177–4183 (1987)). *Pseudomonas* plasmids are reviewed by John et al., (*Rad. Insec. Dis.* 8:693–704 (1986)), and Igaki, (*Jpn. J. Bacteriol.* 33:729–742 (1978)). Broad-host range plasmids or cosmids, such as pCP13 (Darzins and Chakrabarbary, *J. Bacteriol.* 159:9–18, 1984) can also be used for the present invention. The preferred vectors for cloning the genes of the present invention are prokaryotic vectors. Preferably, pCP13 and pUC vectors are used to clone the genes of the present invention.

The preferred host for cloning the reverse transcriptase genes of interest is a prokaryotic host. The most preferred prokaryotic host is *E. coli*. However, the desired reverse transcriptase genes of the present invention may be cloned in other prokaryotic hosts including, but not limited to, *Escherichia, Bacillus, Streptomyces, Pseudomonas, Salmonella, Serratia,* and *Proteus.* Bacterial hosts of particular interest include *E. coli* DH10B, which may be obtained from Life Technologies, a Division of Invitrogen Corporation (Rockville, Md.).

Eukaryotic hosts for cloning and expression of the reverse transcriptase of interest include yeast, fungi, and mammalian cells. Expression of the desired reverse transcriptase in such eukaryotic cells may require the use of eukaryotic regulatory regions which include eukaryotic promoters. Cloning and expressing the reverse transcriptase gene in eukaryotic cells may be accomplished by well known techniques using well known eukaryotic vector systems.

Once a DNA library has been constructed in a particular vector, an appropriate host is transformed by well known techniques. Transformed colonies are plated at a density of approximately 200–300 colonies per petri dish. For selection of reverse transcriptase, colonies are then screened for the expression of a reverse transcriptase as described in the Examples below. Briefly, overnight cultures of individual transformant colonies are assayed directly for RT using a labeled deoxynucleotide and analyzed for the presence of labeled product. If RT activity is detected, the mutant is sequenced to determine which amino acids maintained detectable RT activity. The gene encoding a reverse transcriptase of the present invention can be cloned using techniques known to a person in the art.

Modifications or Mutations of Polymerases

Preferably, the polymerase domain, i.e. fingers, palm, thumb regions, as defined herein, specifically those amino acids which are in the area or areas that controls the template, primer, or nucleotide interaction of the reverse transcriptase of interest is modified or mutated in such a way as to produce a mutated or modified reverse transcriptase having increased or enhanced fidelity (decreased misincorporation rate) and/or decreased TdT activity. Modifications or mutations may also be made in other regions in accordance with the invention. One or more mutations may be made in any reverse transcriptase in order to increase fidelity or decrease the TdT activity of the enzyme in accordance with the invention. Such mutations include point mutations, frame shift mutations, deletions and insertions. Preferably, one or more point mutations, resulting in one or more amino acid substitutions, are used to produce reverse trancriptases having enhanced or increased fidelity or decreased or eliminated TdT activity. The numbering of amino acids in the M-MLV reverse transcriptase is based on the mature peptide, in which the N-terminal methionine has been proteolytically removed. In a preferred aspect of the invention, one or more mutations at positions equivalent or corresponding to position Y64, R116, D152, Q190, T197, D124, H126, Y133 and V223 of M-MLV may be made to produce RTs with increased fidelity. Most preferably, a mutation at position T197 within the palm domain of the polymerase results in reverse transcriptases having increased fidelity and/or reduced misincorporation rate. In another aspect of the invention, one or more mutations at positions equivalent or corresponding to F309, T197 or Y133 may be made to produce RTs with decreased or eliminated TdT activity. In this preferred aspect, amino acid substitutions are made at one or more of the above identified positions. Thus, the amino acids at these positions may be substituted with any other amino acid including Ala, Asn, Asp, Cys, Gln, Glu, Gly, His, Ile, Leu, Lys, Met, Phe, Pro, Ser, Thr, Trp, Tyr, and Val.

The corresponding positions of M-MLV RT identified above may be readily identified for other reverse transcriptases by one with skill in the art. Thus, given the defined region and the assays described in the present application, one with skill in the art can make one or a number of modifications which would result in increased fidelity of any reverse trancriptase of interest. The following table illustrates identified regions of interest for known reverse trancriptases.

TABLE 1

| Reverse transcriptase | Sequence locations of high fidelity mutants |
| --- | --- |
| M-MLV | Y64, R116, K152, Q190, T197, V223, D124, H126, Y133 |
| AMV | W25, R76, K110, Q149, T156, M182 |
| RSV | W25, R76, K110, Q149, T156, M182 |
| HIV | W24, R78, G112, Q151, A158, M184 |

The nucleotide sequence for M-MLV (Shinnick et al. *Nature* 293: 543 (1981)), AMV (Joliot et al. *Virology* 195: 812 (1993)), RSV (Haseltine et al. *Proc. Natl. Acad. Sci. USA* 74: 989 (1977)), and HIV (Wong-Staal et al. *Nature* 313: 277 (1985)) is known.

The invention also relates to reverse transcriptase mutants, where the mutations or substitutions have been made in a recognized region of the reverse transcriptase enzyme. Such regions include, but are not limited to, the fingers, palm and/or thumb regions (or combinations therof). In a preferred embodiment of the invention, the mutations or substitutions are made in the thumb region, mutations in which have been shown to decrease the incidence of frame shifting. Methods for measuring the frame shifting rate are described in the examples.

Amino acids that may be substituted for Tyr include Lys, Arg, His, Asp, Glu, Ala, Val, Leu, Ile, Pro, Met, Trp, Gly, Ser, Thr, Cys, Asn or Gln. Amino acids that may be substituted for Arg include Tyr, His, Asp, Glu, Ala, Val, Leu, Ile, Pro, Met, Trp, Gly, Ser, Thr, Cys, Phe, Asn or Gin. Amino acids that may be substituted for Lys include Tyr, Arg, His, Asp, Glu, Ala, Val, Leu, Ile, Pro, Met, Trp, Gly, Ser, Thr, Cys, Asn or Gln. Amino acids that may be substituted for Glu include Lys, Arg, His, Asp, Tyr, Ala, Val, Leu, Ile, Pro, Met, Trp, Gly, Ser, Thr, Cys, Asn or Gln. Amino acids that may be substituted for Thr include Lys, Arg, His, Asp, Glu, Ala, Val, Leu, Ile, Pro, Met, Trp, Gly, Ser, Tyr, Cys, Asn or Gln. Amino acids that may be substituted for Val or include Lys, Arg, His, Asp, Glu, Ala, Tyr, Leu, lle, Pro, Met, Trp, Gly, Ser, Thr, Cys, Asn or Gln. Such mutants may be prepared by well known methods of site directed mutagenesis and as described herein.

Preferably, oligonucleotide directed mutagenesis is used to create the mutant reverse transcriptases which allows for all possible classes of base pair changes at any determined site along the encoding DNA molecule. In general, this technique involves annealing an oligonucleotide complementary (except for one or more mismatches) to a single stranded nucleotide sequence coding for the reverse trancriptase of interest. The mismatched oligonucleotide is then extended by DNA polymerase, generating a double stranded DNA molecule which contains the desired change in sequence on one strand. The changes in sequence can of course result in the deletion, substitution, or insertion of an amino acid. The double stranded polynucleotide can then be inserted into an appropriate expression vector, and a mutant polypeptide can thus be produced. The above-described oligonucleotide directed mutagenesis can of course be carried out via PCR.

Enhancing Expression of Reverse Transcriptases

To optimize expression of the reverse transcriptases of the present invention, inducible or constitutive promoters are well known and may be used to express high levels of a reverse transcriptase structural gene in a recombinant host. Similarly, high copy number vectors, well known in the art, may be used to achieve high levels of expression. Vectors having an inducible high copy number may also be useful to enhance expression of the reverse transcriptases of the invention in a recombinant host.

To express the desired structural gene in a prokaryotic cell (such as, *E. coli, B. subtilis, Pseudomonas*, etc.), it is necessary to operably link the desired structural gene to a functional prokaryotic promoter. However, the natural promoter of the reverse transcriptase gene may function in prokaryotic hosts allowing expression of the reverse transcriptase gene. Thus, the natural promoter or other promoters may be used to express the reverse trancriptase gene. Such other promoters that may be used to enhance expression include constitutive or regulatable (i.e., inducible or derepressible) promoters. Examples of constitutive promoters include the int promoter of bacteriophage 1, and the bla promoter of the β-lactamase gene of pBR322. Examples of inducible prokaryotic promoters include the major right and left promoters of bacteriophage 1 ($P_R$ and $P_L$), trp, recA, lacZ, lac, tet, gal, trc, and tac promoters of *E. coli*. The *B. subtilis* promoters include α-amylase (Ulmanen et al, *J. Bacteriol* 162:176–182 (1985)) and *Bacillus* bacteriophage promoters (Gryczan, T., In: *The Molecular Biology Of Bacilli*, Academic Press, New York (1982)). *Streptomyces* promoters are described by Ward et al., *Mol. Gen. Genet.* 203:468478 (1986)). Prokaryotic promoters are also reviewed by Glick, *J. Ind. Microbiol.* 1:277–282 (1987); Cenatiempto, Y., *Biochimie* 68:505–516 (1986); and Gottesman, *Ann. Rev. Genet.* 18:415–442 (1984). Expression in a prokaryotic cell also requires the presence of a ribosomal binding site upstream of the gene-encoding sequence. Such ribosomal binding sites are disclosed, for example, by Gold et al., *Ann. Rev. Microbiol.* 35:365404 (1981).

To enhance the expression of polymerases of the invention in a eukaryotic cell, well known eukaryotic promoters and hosts may be used. Preferably, however, enhanced expression of the polymerases is accomplished in a prokaryotic host. The preferred prokaryotic host for overexpressing this enzyme is *E. coli*.

Isolation and Purification of Reverse Transcriptases

The enzyme(s) of the present invention is preferably produced by fermentation of the recombinant host containing and expressing the desired reverse transcriptase gene. However, the reverse transcriptase of the present invention may be isolated from any strain which produces the reverse transcriptase of the present invention. Fragments of the reverse transcriptase are also included in the present invention. Such fragments include proteolytic fragments and fragments having reverse transcriptase activity.

Any nutrient that can be assimilated by a host containing the cloned reverse transcriptase gene may be added to the culture medium. Optimal culture conditions should be selected case by case according to the strain used and the composition of the culture medium. Antibiotics may also be added to the growth media to insure maintenance of vector DNA containing the desired gene to be expressed. Media formulations have been described in DSM or ATCC Catalogs and Sambrook et al., In: *Molecular Cloning, a Laboratory Manual* (2nd ed.), Cold Spring Harbor Laboratory Press, Cold Spring Harbor, N.Y. (1989).

Recombinant host cells producing the reverse transcriptases of this invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation or centrifugation, the reverse transcriptases can be purified by standard protein purification techniques such as extraction, precipitation, chromatography, affinity chromatography, electrophoresis or the like. Assays to detect the presence of the reverse transcriptase during purification are well known in the art and can be used during conventional biochemical purification methods to determine the presence of these enzymes.

The reverse transcriptases of the invention preferably have specific DNA polymerase activities greater than about 5 units/mg, more preferably greater than about 50 units/mg, still more preferably greater than about 100 units/mg, 250 units/mg, 500 units/mg, 1000 units/mg, 5000 units/mg or 10,000 units/mg, and most preferably greater than about 15,000 units/mg, greater than about 16,000 units/mg, greater than about 17,000 units/mg, greater than about 18,000 units/mg, greater than about 19,000 units/mg and greater than about 20,000 units/mg. Preferred ranges of specific activities for the RTs of the invention include a specific activity from about 5 units/mg to about 140,000 units/mg, a specific activity from about 5 units/mg to about 125,000 units/mg, a specific activity of from about 50 units/mg to about 100,000 units/mg, a specific activity from about 100 units/mg to about 100,000 units/mg, a specific activity from about 250 units/mg to about 100,000 units/mg, a specific activity from about 500 units/mg to about 100,000 units/mg, a specific activity from about 1000 units/mg to about 100,000 units/mg, a specific activity from about 5000 units/mg to about 100,000 units/mg, a specific activity from about 10,000 units/mg to about 100,000 units/mg, a specific activity from about 25,000 units/mg to about 75,000 units/mg. Other preferred ranges of specific activities include a specific activity of from about 20,000 units/mg to about 140,000 units/mg, a specific activity from about 20,000 units/mg to about 130,000 units/mg, a specific activity from about 20,000 units/mg to about 120,000 units/mg, a specific activity from about 20,000 units/mg to about 110,000 units/mg, a specific activity from about 20,000 units/mg to about 100,000 units/mg, a specific activity from about 20,000 units/mg to about 90,000 units/mg, a specific activity from about 25,000 units/mg to about 140,000 units/mg, a specific activity from about 25,000 units/mg to about 130,000 units/mg, a specific activity from about 25,000 units/mg to about 120,000 units/mg, a specific activity from about 25,000 units/mg to about 110,000 units/mg, a specific activity from about 25,000 units/mg to about 100,000 units/mg, and a specific activity from about 25,000 units/mg to about 90,000 units/mg. Preferably, the lower end of the specific activity range may vary from 30,000, 35,000, 40,000, 45,000, 50,000, 5,000, 60,000, 65,000, 70,000, 75,000, and 80,000 units/mg, while the upper end of the range may vary from 150,000, 140,000, 130,000, 120,000, 110,000, 100,000, and 90,000 units/mg. In accordance with the invention, specific activity is a measurement of the enzymatic activity (in units) of the protein or enzyme relative to the total amount of protein or enzyme used in a reaction. The measurement of a specific activity may be determined by standard techniques well-known to one of ordinary skill in the art.

The RTs of the invention may be used to make nucleic acid molecules from one or more templates. Such methods comprise mixing one or more nucleic acid templates (e.g., mRNA, and more preferably a population of mRNA molecules) with one or more of the RTs of the invention and incubating the mixture under conditions sufficient to make one or more nucleic acid molecules complementary to all or a portion of the one or more nucleic acid templates.

The invention also relates to methods for the amplification of one or more nucleic acid molecules comprising mixing one or more nucleic acid templates with one of the RTs of the invention, and incubating the mixture under conditions sufficient to amplify one or more nucleic acid molecules complementary to all or a portion of the one or more nucleic acid templates.

The invention also concerns methods for the sequencing of one or more nucleic acid molecules comprising (a) mixing one or more nucleic acid molecules to be sequenced with one or more primer nucleic acid molecules, one or more RTs of the invention, one or more nucleotides and one or more terminating agents; (b) incubating the mixture under conditions sufficient to synthesize a population of nucleic acid molecules complementary to all or a portion of the one or more nucleic acid molecules to be sequenced; and (c) separating the population of nucleic acid molecules to determine the nucleotide sequence of all or a portion of the one or more nucleic acid molecules to be sequenced.

The invention also concerns nucleic acid molecules produced by such methods (which may be full-length cDNA molecules), vectors (particularly expression vectors) comprising these nucleic acid molecules and host cells comprising these vectors and nucleic acid molecules.

Sources of DNA Polymerase

A variety of DNA polymerases are useful in accordance with the present invention. Such polymerases include, but are not limited to, *Thermus thermophilus* (Tth) DNA polymerase, *Thermus aquaticus* (Taq) DNA polymerase, *Thermotoga neapolitana* (Tne) DNA polymerase, *Thermotoga maritima* (Tma) DNA polymerase, *Thermococcus litoralis* (Tli or VENT™) DNA polymerase, *Pyrococcus furiosis* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, *Mycobacterium* spp. DNA polymerase (Mtb, Mlep), and mutants, variants and derivatives thereof.

DNA polymerases used in accordance with the invention may be any enzyme that can synthesize a DNA molecule from a nucleic acid template, typically in the 5' to 3' direction. Such polymerases may be mesophilic or thermophilic, but are preferably thermophilic. Mesophilic polymerases include T5 DNA polymerase, T7 DNA polymerase, Klenow fragment DNA polymerase, DNA polymerase III, and the like. Preferred DNA polymerases are thermostable DNA polymerases such as Taq, Tne, Tma, Pfu, VENT™, DEEPVENT™, Tth and mutants, variants and derivatives thereof (U.S. Pat. No. 5,436,149; U.S Pat. No. 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J.-M., et al., *Nucl. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Barnes, W. M., *Gene* 112:29–35 (1992); and commonly owned, co-pending U.S. patent application Ser. No. 09/741,664, filed Dec. 21, 2000, and corresponding European Application 0942917, the disclosures of all of which are incorporated herein in their entireties. Examples of DNA polymerases substantially lacking in 3' exonuclease activity include, but are not limited to, Taq, Tne(exo⁻), Tma, Pfu (exo⁻), Pwo and Tth DNA polymerases, and mutants, variants and derivatives thereof. Nonlimiting examples of DNA polymerases having 3' exonuclease activity include Pfu/DEEPVENT™ and Tli/VENT™ and mutants, variants and derivatives thereof.

Formulation of Enzyme Compositions

To form the compositions of the present invention, one or more reverse transcriptases are preferably admixed in a buffered salt solution. One or more DNA polymerases and/or one or more nucleotides, and/or one or more primers may optionally be added to make the compositions of the invention. More preferably, the enzymes are provided at working concentrations in stable buffered salt solutions. The terms "stable" and "stability" as used herein generally mean the retention by a composition, such as an enzyme composition, of at least 70%, preferably at least 80%, and most preferably at least 90%, of the original enzymatic activity (in units) after the enzyme or composition containing the enzyme has been stored for about one week at a temperature of about 4° C., about two to six months at a temperature of about –20° C., and about six months or longer at a temperature of about –80° C. As used herein, the term "working concentration" means the concentration of an enzyme that is at or near the optimal concentration used in a solution to perform a particular function (such as reverse transcription of nucleic acids).

The water used in forming the compositions of the present invention is preferably distilled, deionized and sterile filtered (through a 0.1–0.2 micrometer filter), and is free of contamination by DNase and RNase enzymes. Such water is available commercially, for example from Sigma Chemical Company (Saint Louis, Mo.), or may be made as needed according to methods well known to those skilled in the art.

In addition to the enzyme components, the present compositions preferably comprise one or more buffers and cofactors necessary for synthesis of a nucleic acid molecule such as a cDNA molecule. Particularly preferred buffers for use in forming the present compositions are the acetate, sulfate, hydrochloride, phosphate or free acid forms of Tris-(hydroxymethyl)aminomethane (TRIS®), although alternative buffers of the same approximate ionic strength and pKa as TRIS® may be used with equivalent results. In addition to the buffer salts, cofactor salts such as those of potassium (preferably potassium chloride or potassium acetate) and magnesium (preferably magnesium chloride or magnesium acetate) are included in the compositions. Addition of one or more carbohydrates and/or sugars to the compositions and/or synthesis reaction mixtures may also be advantageous, to support enhanced stability of the compositions and/or reaction mixtures upon storage. Preferred such carbohydrates or sugars for inclusion in the compositions and/or synthesis reaction mixtures of the invention include, but are not limited to, sucrose, trehalose, and the like. Furthermore, such carbohydrates and/or sugars may be added to the storage buffers for the enzymes used in the production of the enzyme compositions and kits of the invention. Such carbohydrates and/or sugars are commercially available from a number of sources, including Sigma (St. Louis, Mo.).

It is often preferable to first dissolve the buffer salts, cofactor salts and carbohydrates or sugars at working concentrations in water and to adjust the pH of the solution prior to addition of the enzymes. In this way, the pH-sensitive enzymes will be less subject to acid- or alkaline-mediated inactivation during formulation of the present compositions.

To formulate the buffered salts solution, a buffer salt which is preferably a salt of Tris(hydroxymethyl)aminomethane (TRIS®), and most preferably the hydrochloride salt thereof, is combined with a sufficient quantity of water to yield a solution having a TRIS® concentration of 5–150 millimolar, preferably 10–60 millimolar, and most preferably about 20–60 millimolar. To this solution, a salt of magnesium (preferably either the chloride or acetate salt thereof) may be added to provide a working concentration thereof of 1–10 millimolar, preferably 1.5–8.0 millimolar, and most preferably about 3–7.5 millimolar. A salt of potassium (preferably a chloride or acetate salt of potassium) may also be added to the solution, at a working concentration of 10–100 millimolar and most preferably about 75 millimolar. A reducing agent such as dithiothreitol may be added to the solution, preferably at a final concentration of about 1–100 mM, more preferably a concentration of about 5–50 mM or about 7.5–20 mM, and most preferably at a concentration of about 10 mM. Preferred concentrations of carbohydrates and/or sugars for inclusion in the compositions of the invention range from about 5% (w/v) to about 30% (w/v), about 7.5% (w/v) to about 25% (w/v), about 10% (w/v) to about 25% (w/v), about 10% (w/v) to about 20% (w/v), and preferably about 10% (w/v) to about 15% (w/v). A small amount of a salt of ethylenediaminetetraacetate (EDTA), such as disodium EDTA, may also be added (preferably about 0.1 millimolar), although inclusion of EDTA does not appear to be essential to the function or stability of the compositions of the present invention. After addition of all buffers and salts, this buffered salt solution is mixed well until all salts are dissolved, and the pH is adjusted using methods known in the art to a pH value of 7.4 to 9.2, preferably 8.0 to 9.0, and most preferably about 8.4.

To these buffered salt solutions, the enzymes (reverse transcriptases and/or DNA polymerases) are added to produce the compositions of the present invention. M-MLV RTs are preferably added at a working concentration in the solution of about 1,000 to about 50,000 units per milliliter, about 2,000 to about 30,000 units per milliliter, about 2,500 to about 25,000 units per milliliter, about 3,000 to about 22,500 units per milliliter, about 4,000 to about 20,000 units per milliliter, and most preferably at a working concentration of about 5,000 to about 20,000 units per milliliter. AMV RTs, RSV RTs and HIV RTs, including those of the invention described above, are preferably added at a working concentration in the solution of about 100 to about 5000 units per milliliter, about 125 to about 4000 units per milliliter, about 150 to about 3000 units per milliliter, about 200 to about 2500 units per milliliter, about 225 to about 2000 units per milliliter, and most preferably at a working concentration of about 250 to about 1000 units per milliliter. The enzymes in the thermophilic DNA polymerase group (Taq, Tne, Tma, Pfu, VENT, DEEPVENT, Tth and mutants, variants and derivatives thereof) are preferably added at a working concentration in the solution of about 100 to about 1000 units per milliliter, about 125 to about 750 units per milliliter, about 150 to about 700 units per milliliter, about 200 to about 650 units per milliliter, about 225 to about 550 units per milliliter, and most preferably at a working concentration of about 250 to about 500 units per milliliter. The enzymes may be added to the solution in any order, or may be added simultaneously.

The compositions of the invention may further comprise one or more nucleotides, which are preferably deoxynucleoside triphosphates (dNTPs) or dideoxynucleoside triphosphates (ddNTPs). The dNTP components of the present compositions serve as the "building blocks" for newly synthesized nucleic acids, being incorporated therein by the action of the polymerases, and the ddNTPs may be used in sequencing methods according to the invention. Examples of nucleotides suitable for use in the present compositions include, but are not limited to, dUTP, dATP, dTTP, dCTP, dGTP, dITP, 7-deaza-dGTP, α-thio-dATP, α-thio-dTTP, α-thio-dGTP, α-thio-dCTP, ddUTP, ddATP, ddTTP, ddCTP, ddGTP, ddITP, 7-deaza-ddGTP, α-thio-ddATP, α-thio-ddTTP, α-thio-ddGTP, α-thio-ddCTP or derivatives thereof, all of which are available commercially from sources including Life Technologies, a Division of Invitrogen Corporation (Rockville, Md.), New England BioLabs (Beverly, Mass.) and Sigma Chemical Company (Saint Louis, Mo.). The nucleotides may be unlabeled, or they may be detectably labeled by coupling them by methods known in the art with radioisotopes (e.g., $^3$H, $^{14}$C, $^{32}$P or $^{35}$S), vitamins (e.g., biotin), fluorescent moieties (e.g., fluorescein, rhodamine, Texas Red, or phycoerythrin), chemiluminescent labels (e.g., using the PHOTO-GENE™ or ACES™ chemiluminescence systems, available commercially from Life Technologies, a Division of Invitrogen Corporation, Rockville, Md.), dioxigenin and the like. Labeled nucleotides may also be obtained commercially, for example from Life Technologies, a Division of Invitrogen Corporation (Rockville, Md.) or Sigma Chemical Company (Saint Louis, Mo.). In the present compositions, the nucleotides are added to give a working concentration of each nucleotide of about 10–4000 micromolar, about 50–2000 micromolar, about 100–1500 micromolar, or about 200–1200 micromolar, and most preferably a concentration of about 1000 micromolar.

To reduce component deterioration, storage of the reagent compositions is preferably at about 4° C. for up to one day, or most preferably at −20° C. for up to one year.

In another aspect, the compositions and reverse transcriptases of the invention may be prepared and stored in dry form in the presence of one or more carbohydrates, sugars, or synthetic polymers. Preferred carbohydrates, sugars or polymers for the preparation of dried compositions or reverse transcriptases include, but are not limited to, sucrose, trehalose, and polyvinylpyrrolidone (PVP) or combinations thereof. See, e.g., U.S. Pat. Nos. 5,098,893, 4,891,319, and 5,556,771, the disclosures of which are entirely incorporated herein by reference. Such dried compositions and enzymes may be stored at various temperatures for extended times without significant deterioration of enzymes or components of the compositions of the invention. Preferably, the dried reverse transcriptases or compositions are stored at 4° C. or at −20° C.

Production of cDNA Molecules

Sources of Nucleic Acid Molecules

In accordance with the invention, cDNA molecules (single-stranded or double-stranded) may be prepared from a variety of nucleic acid template molecules. Preferred nucleic acid molecules for use in the present invention include single-stranded or double-stranded DNA and RNA molecules, as well as double-stranded DNA:RNA hybrids. More preferred nucleic acid molecules include messenger RNA (mRNA), transfer RNA (tRNA) and ribosomal RNA (rRNA) molecules, although mRNA molecules are the preferred template according to the invention.

The nucleic acid molecules that are used to prepare eDNA molecules according to the methods of the present invention may be prepared synthetically according to standard organic chemical synthesis methods that will be familiar to one of ordinary skill. More preferably, the nucleic acid molecules may be obtained from natural sources, such as a variety of cells, tissues, organs or organisms. Cells that may be used as sources of nucleic acid molecules may be prokaryotic (bacterial cells, including but not limited to those of species of the genera *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas* and *Streptomyces*) or eukaryotic (including fungi (especially yeasts), plants, protozoans and other parasites, and animals including insects (particularly *Drosophila* spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid molecules (such as mRNA) may be isolated therefrom by methods that are well-known in the art (See, e.g., Maniatis, T., et al., *Cell* 15:687–701 (1978); Okayama, H., and Berg, P., *Mol. Cell. Biol.* 2:161–170 (1982); Gubler, U., and Hoffman, B. J., *Gene* 25:263–269 (1983)). The nucleic acid molecules thus isolated may then be used to prepare cDNA molecules and cDNA libraries in accordance with the present invention.

In the practice of the invention, cDNA molecules or cDNA libraries are produced by mixing one or more nucleic acid molecules obtained as described above, which is preferably one or more mRNA molecules such as a population of mRNA molecules, with a polypeptide having reverse transcriptase activity of the present invention, or with one or more of the compositions of the invention, under conditions favoring the reverse transcription of the nucleic acid molecule by the action of the enzymes or the compositions to form a cDNA molecule (single-stranded or double-stranded). Thus, the method of the invention comprises (a) mixing one or more nucleic acid templates (preferably one or more RNA or mRNA templates, such as a population of mRNA molecules) with one or more reverse transcriptases of the invention and (b) incubating the mixture under conditions sufficient to make one or more nucleic acid molecules complementary to all or a portion of the one or more templates. Such methods may include the use of one or more DNA polymerases, one or more nucleotides, one or more primers, one or more buffers, and the like. The invention may be used in conjunction with methods of cDNA synthesis such as those described in the Examples below, or others that are well-known in the art (see, e.g., Gubler, U., and Hoffman, B. J., *Gene* 25:263–269 (1983); Krug, M. S., and Berger, S. L., *Meth. Enzymol.* 152:316–325 (1987); Sambrook, J., et al., *Molecular Cloning: A Laboratory Manual*, 2nd ed., Cold Spring Harbor, N.Y.: Cold Spring Harbor Laboratory Press, pp. 8.60–8.63 (1989); WO 99/15702; WO 98/47912; and WO 98/51699), to produce cDNA molecules or libraries.

Other methods of cDNA synthesis which may advantageously use the present invention will be readily apparent to one of ordinary skill in the art.

Having obtained cDNA molecules or libraries according to the present methods, these cDNAs may be isolated for further analysis or manipulation. Detailed methodologies for purification of cDNAs are taught in the GENETRAPPER™ manual (Life Technologies, a Division of Invitrogen Corporation, Rockville, Md.), which is incorporated herein by reference in its entirety, although alternative standard techniques of cDNA isolation that are known in the art (see, e.g., Sambrook, J., et al., *Molecular Cloning: A Laboratory Manual*, 2nd ed., Cold Spring Harbor, N.Y.: Cold Spring Harbor Laboratory Press, pp. 8.60–8.63 (1989)) may also be used.

In other aspects of the invention, the invention may be used in methods for amplifying and sequencing nucleic acid molecules. Nucleic acid amplification methods according to this aspect of the invention may be one-step (e.g., one-step RT-PCR) or two-step (e.g., two-step RT-PCR) reactions. According to the invention, one-step RT-PCR type reactions may be accomplished in one tube thereby lowering the possibility of contamination. Such one-step reactions comprise (a) mixing a nucleic acid template (e.g., mRNA) with one or more reverse transcriptases of the present invention and with one or more DNA polymerases and (b) incubating the mixture under conditions sufficient to amplify a nucleic acid molecule complementary to all or a portion of the template. Such amplification may be accomplished by the reverse transcriptase activity alone or in combination with the DNA polymerase activity. Two-step RT-PCR reactions may be accomplished in two separate steps. Such a method comprises (a) mixing a nucleic acid template (e.g., mRNA) with a reverse transcriptase of the present invention, (b) incubating the mixture under conditions sufficient to make a nucleic acid molecule (e.g., a DNA molecule) complementary to all or a portion of the template, (c) mixing the nucleic acid molecule with one or more DNA polymerases and (d) incubating the mixture of step (c) under conditions sufficient to amplify the nucleic acid molecule. For amplification of long nucleic acid molecules (i.e., greater than about 3–5 Kb in length), a combination of DNA polymerases may be used, such as one DNA polymerase having 3' exonuclease activity and another DNA polymerase being substantially reduced in 3' exonuclease activity.

Nucleic acid sequencing methods according to this aspect of the invention may comprise both cycle sequencing (sequencing in combination with amplification) and standard sequencing reactions. The sequencing method of the invention thus comprises (a) mixing a nucleic acid molecule to be sequenced with one or more primers, one or more reverse transcriptase of the invention, one or more nucleotides and one or more terminating agents, (b) incubating the mixture under conditions sufficient to synthesize a population of nucleic acid molecules complementary to all or a portion of the molecule to be sequenced, and (c) separating the population to determine the nucleotide sequence of all or a portion of the molecule to be sequenced. According to the invention, one or more DNA polymerases (preferably thermostable DNA polymerases) may be used in combination with or separate from the reverse transcriptases of the invention.

Amplification methods which may be used in accordance with the present invention include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822), as well as more complex PCR-based nucleic acid fingerprinting techniques such as Random Amplified Polymorphic DNA (RAPD) analysis (Williams, J. G. K., et al., *Nucl. Acids Res.* 18(22):6531–6535, 1990), Arbitrarily Primed PCR (AP-PCR; Welsh, J., and McClelland, M., *Nucl. Acids Res.* 18(24):7213–7218, 1990), DNA Amplification Fingerprinting (DAF; Caetano-Anollés et al., *Bio/Technology* 9:553–557, 1991), microsatellite PCR or Directed Amplification of Minisatellite-region DNA (DAMD; Heath, D. D., et al. *Nucl. Acids Res.* 21 (24): 5782–5785 (1993), and Amplification Fragment Length Polymorphism (AFLP) analysis (EP 0 534 858; Vos, P., et al. *Nucl. Acids Res.* 23(21):4407–4414 (1995); Lin, J. J., and Kuo, J. *FOCUS* 17(2):66–70 (1995). Nucleic acid sequencing techniques which may employ the present compositions include dideoxy sequencing methods such as those disclosed in U.S. Pat. Nos. 4,962,022 and 5,498,523. In a particularly preferred aspects, the invention may be used in methods of amplifying or sequencing a nucleic acid molecule comprising one or more polymerase chain reactions (PCRs), such as any of the PCR-based methods described above.

Kits

In another embodiment, the present invention may be assembled into kits for use in reverse transcription or amplification of a nucleic acid molecule, or into kits for use in sequencing of a nucleic acid molecule. Kits according to this aspect of the invention comprise a carrier means, such as a box, carton, tube or the like, having in close confinement therein one or more container means, such as vials, tubes, ampules, bottles and the like, wherein a first container means contains one or more polypeptides of the present invention having reverse transcriptase activity. When more than one polypeptide having reverse transcriptase activity is used, they may be in a single container as mixtures of two or more polypeptides, or in separate containers. The kits of the invention may also comprise (in the same or separate containers) one or more DNA polymerases, a suitable buffer, one or more nucleotides and/or one or more primers.

In a specific aspect of the invention, the reverse transcription and amplification kits may comprise one or more components (in mixtures or separately) including one or more polypeptides having reverse transcriptase activity of the invention, one or more nucleotides needed for synthesis of a nucleic acid molecule, and/or one or more primers (e.g., oligo(dT) for reverse transcription). Such reverse transcription and amplification kits may further comprise one or more DNA polymerases. Sequencing kits of the invention may comprise one or more polypeptides having reverse transcriptase activity of the invention, and optionally one or more DNA polymerases, one or more terminating agents (e.g., dideoxynucleoside triphosphate molecules) needed for sequencing of a nucleic acid molecule, one or more nucleotides and/or one or more primers. Preferred polypeptides having reverse transcriptase activity, DNA polymerases, nucleotides, primers and other components suitable for use in the reverse transcription, amplification and sequencing kits of the invention include those described above. The kits encompassed by this aspect of the present invention may further comprise additional reagents and compounds necessary for carrying out standard nucleic acid reverse transcription, amplification or sequencing protocols. Such polypeptides having reverse transcriptase activity of the invention, DNA polymerases, nucleotides, primers, and additional reagents, components or compounds may be contained in one or more containers, and may be contained in such containers in a mixture of two or more of the above-noted components or may be contained in the kits of the invention in separate containers.

Use of Nucleic Acid Molecules

The nucleic acid molecules or cDNA libraries prepared by the methods of the present invention may be further characterized, for example by cloning and sequencing (i.e., determining the nucleotide sequence of the nucleic acid molecule), by the sequencing methods of the invention or by others that are standard in the art (see, e.g., U.S. Pat. Nos. 4,962,022 and 5,498,523, which are directed to methods of DNA sequencing). Alternatively, these nucleic acid molecules may be used for the manufacture of various materials in industrial processes, such as hybridization probes by methods that are well-known in the art. Production of hybridization probes from cDNAs will, for example, provide the ability for those in the medical field to examine a patient's cells or tissues for the presence of a particular genetic marker such as a marker of cancer, of an infectious or genetic disease, or a marker of embryonic development. Furthermore, such hybridization probes can be used to isolate DNA fragments from genomic DNA or cDNA libraries prepared from a different cell, tissue or organism for further characterization.

The nucleic acid molecules of the present invention may also be used to prepare compositions for use in recombinant DNA methodologies. Accordingly, the present invention relates to recombinant vectors which comprise the cDNA or amplified nucleic acid molecules of the present invention, to host cells which are genetically engineered with the recombinant vectors, to methods for the production of a recombinant polypeptide using these vectors and host cells, and to recombinant polypeptides produced using these methods.

Recombinant vectors may be produced according to this aspect of the invention by inserting, using methods that are well-known in the art, one or more of the cDNA molecules or amplified nucleic acid molecules prepared according to the present methods into a vector. The vector used in this aspect of the invention may be, for example, a phage or a plasmid, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

In certain preferred embodiments in this regard, the vectors provide for specific expression (and are therefore termed "expression vectors"), which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the cDNA or amplified nucleic acid molecules of the invention should be operatively linked to an appropriate promoter, such as the phage lambda $P_L$ promoter, the *E. coli* lac, trp and tac promoters. Other suitable promoters will be known to the skilled artisan.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen Corporation; pGEX, pTrxfus, pTrc99a, pET-5, pET-9, pKK223–3, pKK233–3, pDR540, pRIT5 available from Pharmacia; and pSPORT1, pSPORT2 and pSV.SPORT1, available from Life Technologies, a Division of Invitrogen Corporation. Other suitable vectors will be readily apparent to the skilled artisan.

The invention also provides methods of producing a recombinant host cell comprising the cDNA molecules, amplified nucleic acid molecules or recombinant vectors of the invention, as well as host cells produced by such methods. Representative host cells (prokaryotic or eukaryotic) that may be produced according to the invention include, but are not limited to, bacterial cells, yeast cells, plant cells and animal cells. Preferred bacterial host cells include *Escherichia coli* cells (most particularly *E. coli* strains DH10B and Stbl2, which are available commercially (Life Technologies, a Division of Invitrogen Corporation; Rockville, Md.)), *Bacillus subtilis* cells, *Bacillus megaterium* cells, *Streptomyces* spp. cells, *Erwinia* spp. cells, *Klebsiella* spp. cells and *Salmonella typhimurium* cells. Preferred animal host cells include insect cells (most particularly *Spodoptera frugiperda* Sf9 and Sf21 cells and *Trichoplusa* High-Five cells) and mammalian cells (most particularly CHO, COS, VERO, BHK and human cells). Such host cells may be prepared by well-known transformation, electroporation or transfection techniques that will be familiar to one of ordinary skill in the art.

In addition, the invention provides methods for producing a recombinant polypeptide, and polypeptides produced by these methods. According to this aspect of the invention, a recombinant polypeptide may be produced by culturing any of the above recombinant host cells under conditions favoring production of a polypeptide therefrom, and isolation of the polypeptide. Methods for culturing recombinant host cells, and for production and isolation of polypeptides therefrom, are well-known to one of ordinary skill in the art.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

The following Materials and Methods were used in the Examples below.

LacZ Forward Assay Using an RNA Template

The assay was conducted as described in Boyer J C, et al. Analyzing the fidelity of reverse transcription and transcription. *Methods Enzymol.* 275: 523 (1996), with the following exceptions.

Preparation of RNA template. A clone of pUC19 (homologous with M13mp19 in lacZ region) with the T7 RNA promoter inserted between nucleotides 112 and 113 was used as the RNA template.

Construction of gapped M13 substrate. M13mp19 (Life Technologies, a Division of Invitrogen Corporation, Rockville, Md.) was used instead of M13mp2.

Preparation of Competent cells. Electromax DH12S competent cells (Life Technologies, a Division of Invitrogen Corporation, Rockville, Md.) were used instead of MC1061.

Mutagenesis. The mutants were made by oligo-directed mutagenesis as described in Kunkel, T. A. et al. *Methods Enzymol.* 204: 125 (1991). Briefly, the Superscript II gene (an M-MLV RT gene containing point mutations in the RNase H domain, see below) was inserted into pBADhisA (Invitrogen, Carlsbad, Calif.) vector and named pBAD-SS II. This plasmid was transformed into DH11S cells (Life Technologies, a Division of Invitrogen Corporation, Rockville, Md.) and infected with M13K07 helper phage from which single strand DNA was isolated. Oligos were designed corresponding to each mutation: Y64W, R116M, K152R, Q190F, T197A, and V223H. 100 µM of each oligo was $^{32}$P-labeled with T4 polynucleotide kinase (Life Technologies, a Division of Invitrogen Corporation, Rockville, Md.) using the Forward Rxn Buffer (Life Technologies, a Division of Invitrogen Corporation, Rockville, Md.). The oligo was annealed to the single strand pBAD-SS II. Native T7 DNA polymerase (USB, Cleveland, Ohio) and T4 DNA ligase (Life Technologies, a Division of Invitrogen Corporation, Rockville, Md.) were added with synthesis buffer (0.4 mM dNTPs, 17.5 mM Tris-HCl, pH 7.5, 5 mM MgCl$_2$, 2.5 mM DTT, and 1 mM ATP) to the annealed reaction on ice. The reactions were incubated at 37° C. for 30 minutes and terminated by adding 1 µl of 0.5 M EDTA (Life Technologies, a Division of Invitrogen Corporation, Rockville, Md.). The reactions were transformed and plated with DH10B cells. Colonies were picked and mutants were determined by restriction analysis and sequenced using an ABI 377 and ABI Big Dye terminator cycle sequencing ready reaction kit (PE Applied Biosystems, Foster City, Calif.) for confirmation.

Protein Purification of mutants. The cell pellet containing induced RT was suspended in a ratio of 2 mL Lysis buffer (40 mM Tris-HCl, pH 8.0, 0.1 M KCl, 1 mM PMSF)/1 gram of cell pellet. The suspension was sonicated on ice and then centrifuged at 27000×g for 30 min. The cell-free extract was filtered through a 0.45µ syringe filter. The cell-free extract was applied to a 5-mL Ni2+ HI-TRAP column (Pharmacia) pre-equilibrated with 5 volumes 5 mM imidazole in Buffer A (40 mM Tris-HCl, pH 8.0, 10% glycerol, 0.01% Triton X-100, 0.1 M KCl) at 1 mL/min. The column was washed with 10 volumes 5 mM imidazole in Buffer A. The RT was eluted by washing with 20 volumes of a gradient of 5 mM to 1 M imidazole in Buffer A. The eluate containing RT protein was applied to a 1-mL Mono-S column (Pharmacia) pre-equilabrated with 10 column volumes 50 mM KCl in Buffer B (40 mM Tris-HCl, pH 8.0, 10% glycerol, 0.01% Triton X-100, 0.1 mM EDTA, 1 mM DTT) at a flow rate of 1.0 mL/min. The column was washed with 10 volumes 50 mM KCl in Buffer B. RT was eluated with 20 volumes of a gradient from 50 mM to 1 M KCl in Buffer B. The individual fractions were analyzed for RT activity. The fraction containing peak RT activity was dialyzed against Storage buffer (40 mM Tris-HCl, pH 8.0, 50% glycerol, 0.01% Triton X-100, 0.1 mM EDTA, 1 mM DTT, 0.1 M KCl). The isolated proteins were more than 95% pure, as judged by SDS-PAGE. The protein concentrations were determined by using the Biorad colorimetric kit with BSA as a standard.

Example 1

Mutation Frequency of M-MLV High Fidelity Mutants

Mutation frequency Data and Calculation of Error Rates. Mutation frequency (MF) is determined by dividing the number of mutant plaques (light blue or white) by the total number of plaques and then subtracting the background mutation frequency of the starting DNA.

All mutant reverse transcriptases tested also contained the point mutations to remove RNase H activity, as in SuperScript II (SS II, U.S. Pat. Nos. 5,244,797; 5,405,776; 5,668,005 and 6,063,608). Point mutations were made in the M-MLV RT gene to remove RNase H activity. The point mutations include D524G, D583N, and E562Q. Briefly, the RT gene from pRT601 was inserted into a pUC plasmid and then the above point mutations were made in the RNase H domain of the RT gene. pRT601 is described in U.S. Pat. Nos. 5,244,797; 5,405,776; 5,668,005 and 6,063,608 and was deposited at the ATCC under Accession No. 67007 (See U.S. Pat. No. 5,017,492). This RNase H$^-$ mutant is referred to herein as SuperScript II or SuperScript II gene.

TABLE 2

| RT | total plaques | mutant plaques | MF (×10$^{-4}$) |
|---|---|---|---|
| AMV | 11195 | 71 | 58 |
| RSV | 11435 | 46 | 35 |
| M-MLV | 10737 | 40 | 32 |
| SS II (H$^-$ RT) | 17771 | 87 | 44 |
| M-MLV Y64W | 9007 | 30 | 28 |
| M-MLV R116M | 9834 | 32 | 28 |
| M-MLV K152R | 13988 | 45 | 27 |
| M-MLV Q190F | 10693 | 26 | 19 |
| M-MLV T197A | 15399 | 50 | 27 |
| M-MLV V223H | 17260 | 46 | 21 |
| M-MLV V223F | 6963 | 71 | 97 |

The lacZα assay employs the provided RT to copy lacZα RNA to cDNA. This cDNA copy, when annealed to M13, transfected, and expressed, will have either the normal wild type phenotype of a dark blue plaque, or, if the RT made a mistake while copying, it will have the mutant phenotype of a light blue or clear plaque. The mistakes could be in the form of insertions, deletions or misincorporations. Any decrease from the mutation frequency of M-MLV RNase H⁻ RT (SuperScript II) by the mutant RTs indicate an increase in fidelity. As shown in TABLE 2, the selected mutants demonstrate a 1.5–2.3 fold decrease in mutation frequency. The mutant V223F has a mutation frequency 2.2 fold higher than SS II and thus has lower fidelity.

Example 2

Misinsertion Assays with DNA Template

Figure 2:
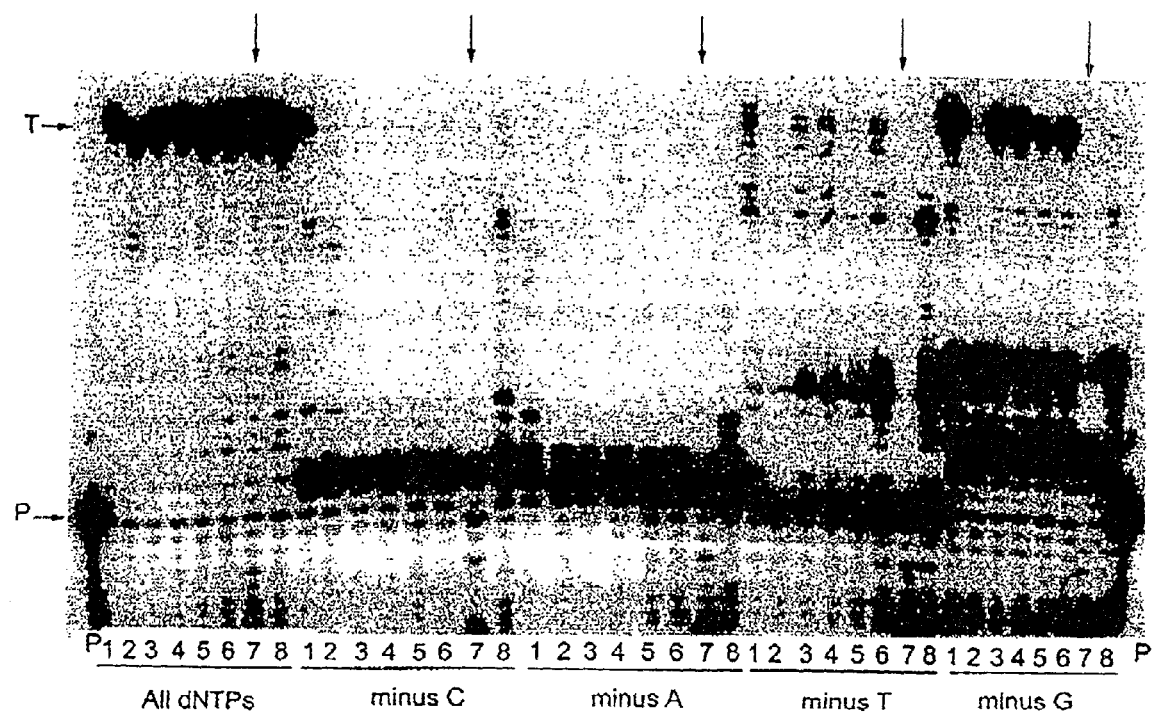
FIG. 2 represents a scanned phosphoimage, which shows misinsertion assay of SuperScript II (1) and mutant R116M (7). Also shown are ThermoScript™ I (2), and SuperScript II mutants F155Y (3), K193T (4), F156H (5), D153N (6), and V223R (8). Reaction conditions same as FIG. 1.
Figure 3:
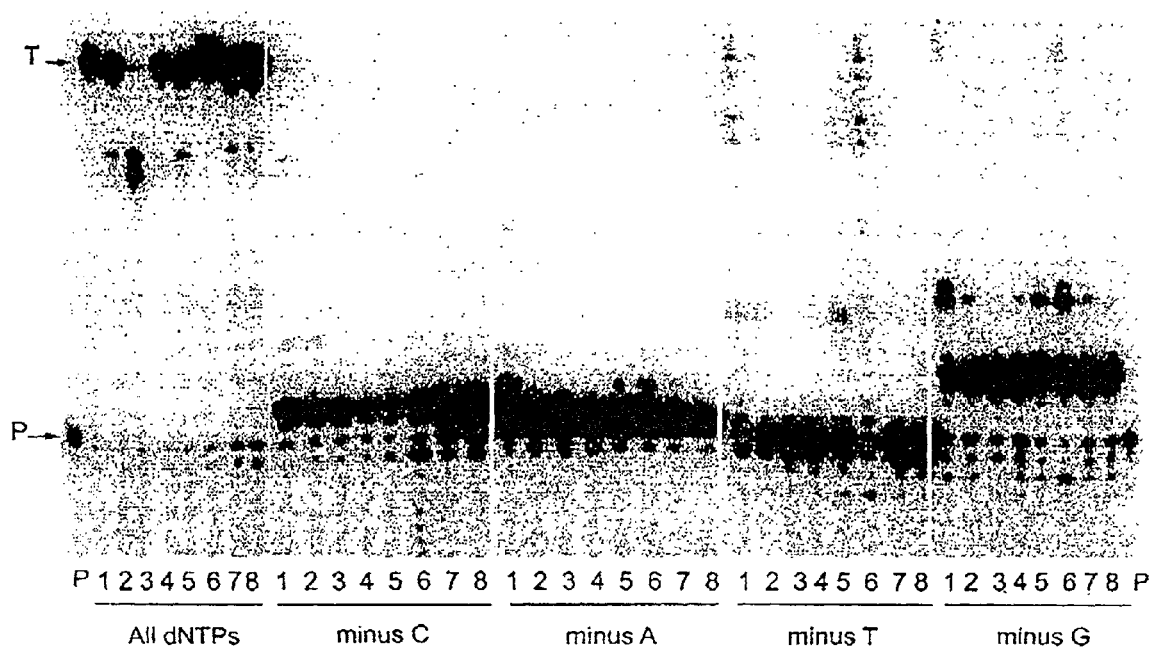
FIG. 3 represents a scanned prophoimage, which shows misinsertion assay of SuperScript II (1), mutants V223H (2), Q190F(4), K152R (5), T197A (7), and Y64W (8), along with mutants V2231 (3) and K193C (6). Reaction conditions same as FIG. 1.

Misinsertion assay of Y64W, R116M, K152R, Q190F, T197A, V223H M-MLV RNase H⁻ RT with DNA template. This assay was employed to compare the misincorporation capability of the mutants to Superscript II (M-MLV RNase H⁻ RT). The assay is a primer extension assay using synthetic DNA template-primer and biased dNTP pools containing only three of the four dNTPs. The reactions are displayed on a gel in FIGS. 1–3. In this assay, higher efficiency of primer extension in the absence of one dNTP denotes lower fidelity. As shown in FIGS. 1–3, in the presence of all 4 dNTPs₃ SuperScript II and all the selected mutants were able to extend the primer approximately equally, with some variance in the addition of non-template nucleotides at the end of the primer. However when incubated with biased pools of nucleotides, SS II was able to catalyze substantial extension past template nucleotides for which a complementary dNTP was missing, indicating use of incorrect nucleotides and lower fidelity. In FIG. 1, the V223H mutant (designated as lane 2) showed shorter extension products than SS II in each of the biased pools of three dNTPs, indicating less ability to incorporate incorrect nucleotides and thus higher fidelity. This corresponds with the results of the lacZα assay where the V223H mutant had a lower mutation frequency than SS II, $21 \times 10^{-4}$ versus $44 \times 10^{-4}$, respectively. On the other hand V223F (lane 3), which had a higher mutation frequency ($97 \times 10^{-4}$) than SS II ($44 \times 10^{-4}$) in the lacZα assay, also has equal sized or longer extension products than SS II in each of the biased pools, indicating that it has a lower fidelity. These data shows a correlation between the misinsertion assay on DNA and the lacZα assay on RNA wherein higher fidelity mutants had both shorter extension products with biased pools of dNTPs and lower mutation frequencies in the lacZα assay. FIG. 2 and FIG. 3 show similar results for the mutants R116M, Q190F, K152R, T197A, and Y64W, where each had shorter primer extension products than SS II in the biased nucleotide pools.

Example 3

TdT Reverse Transcriptase Mutants

In checking fidelity mutants of reverse transcriptase (RT) for misextension in a 3 dNTP assay, it was observed that SS II RT extended 2–3 bases past the end of the template in the presence of 3 and 4 dNTPs. This non-template directed extension or TdT activity is reduced in many mutants, but in a few such as F309N and T197E it appears that this activity is severely reduced or eliminated. These mutants are probably in close proximity or in contact with the template-primer as determined by homology to HIV reverse transcriptase and its crystal structure with bound template-primer.

Methods

Mutagenesis

For F309N:

Primers were designed corresponding to the mutant position F309 with the silent insertion of a NgoMIV restriction site at amino acid positions 310–311. The primers encoded a random NNK sequence for this position generating a random library of F309 mutants, where N is any of the four bases and K is T or G. The primers along with internal SS II RT primers at an upstream SstI restriction site and a downstream SalI restriction site were used in a standard PCR reaction (10 ng SS II RT template, 2 μM of each primer, 48 μl Supermix (Life Technologies, a division of Invitrogen Corporation) for 20 cycles of 94° C. 15 sec, 55° C. 15 sec, 72° C. 30 sec) to generate two PCR fragments. These were a 240 bp SstI-NgoMIV fragment and a 200 bp NgoMIV-SalI fragment. The fragments were isolated and digested and ligated together and then inserted into the original SS II RT clone cut with SstI and SalI. The resulting ligation product was transformed in Max Efficiency DH10B (Life Technologies, a division of Invitrogen Corporation) competent cells to create the library of mutants at site F309. This library was then plated overnight for selection.

For T197E and Y133A:

The mutants T197E and Y133A were made by oligo-directed mutagenesis as described in Kunkel, T. A. et al. *Methods Enzymol.* 204. 125 (1991). Briefly, the SuperScript II RT gene was inserted into pBADhisA (Invitrogen Corporation) vector and named pBAD-SSII. This plasmid was transformed into DH11S cells and the cells were infected with M13K07 helper phage from which single strand DNA was isolated. Oligos were designed corresponding to each mutation: T197E and Y133A. Each oligo (100 μM) was kinased with T4 DNA kinase (Life Technologies, a division of Invitrogen Corporation) using the Forward Rxn Buffer (Life Technologies, a division of Invitrogen Corporation). The oligo was annealed to single stranded pBAD-SSII DNA. Native T7 DNA polymerase (USB) and T4 DNA ligase (Life Technologies, a division of Invitrogen Corporation) were added with synthesis buffer (0.4 mM dNTPs, 17.5 mM Tris-HCl, pH 7.5, 5 mM MgCl₂, 2.5 mM DTT, and 1 mM ATP) to the annealed reaction on ice. The reactions were incubated at 37° C. for 30 minutes and terminated by adding 1 μl of 0.5 M EDTA. The reactions were transformed and plated with DH10B cells. Colonies were picked and mutants were determined by restriction enzyme analysis and sequenced for confirmation using an ABI 377 instrument and ABI Big Dye Terminator Cycle Sequencing Ready Reaction kit.

Selecting Colonies Containing Active RT. Individual transformant colonies were inoculated into single wells of a 96 well culture plate. Each well contained 120 μl of media (EG-Ap) containing 0.2% arabinose. It is preferable to first inoculate a 96 well plate with selective medium without the inducer, to grow that master plate overnight, and then to make a replica of the master plate into a 96-well plate with the inducer and grow that plate overnight. The cultures were grown overnight at 37° C. without shaking. Overnight cultures were mixed with an equal volume of 2× PLD (1.8% glucose, 50 mM Tris-HCl, pH 8.0, 20 mM EDTA, 20 mM DTT, 1% Triton X-100, 2 mg/mL lysozyme) at room temperature. These extracts were assayed directly for RT activity by mixing 10 μl of the extract with 40 μl of 1.25× RT reaction mix (62.5 mM Tris-HCl, pH 8.4, 62.5 mM KCl, 12.5 mM MgCl₂, 12.5 mM DTT, 1.25 mM dGTP, polyC/oligo dG (3.75 mM/1.5 mM in nucleotide), [³²P] dGTP). This reaction was placed in a 37° C. water bath for 10 min. A small aliquot of the reaction mixture (5 μl) was spotted onto a charged nylon membrane (Genescreen+, NEN). The membrane was washed twice with 10%TCA+1% sodium pyrophosphate, rinsed with ethanol, dried, and placed next to a phosphor screen. Radioactive product that had been trapped on the filter was detected by analyzing the screen in a Phosphorimager, using ImageQuant software (Molecular Devices). Candidates were selected if they showed RT activity (radioactivity). These candidates were screened a second time to confirm the phenotype. The confirmed candidates were then sequenced to determine which amino acids maintained detectable RT activity.

Purification of RT Mutants.

The cell pellet containing induced RT was suspended in a ratio of 2 mL Lysis buffer (40 mM Tris-HCl, pH 8.0, 0.1 M KCl, 1 mM PMSF)/1 gram of cell pellet. The suspension was sonicated on ice and then centrifuged at 27,000 g for 30 min. The cell-free extract was filtered through a 0.45μ syringe filter. The cell-free extract was applied to a 5 mL $Ni^{2+}$ HI-TRAP column (Pharmacia) pre-equilibrated with 5 volumes 5 mM imidazole in buffer A (40 mM Tris HCl, pH 8.0, 10% glycerol, 0.01% Triton X-100, 0.1 M KCl) at 1 mL/min. The column was washed with 10 volumes 5 mM imidazole in buffer A. The RT was eluted by washing with 20 volumes of a gradient of 5 mM to 1M imidazole in buffer A. The eluate containing RT protein was applied to a 1 mL Mono-S column (Pharmacia) pre-equilabrated with 10 column volumes 50 mM KCl in buffer B (40 mM Tris-HCl, pH 8.0, 10% glycerol, 0.01% Triton X-100, 0.1 mM EDTA, 1 mM DTT) at a flow rate of 1.0 mL/min. The column was washed with 10 volumes of 50 mM KCl in buffer B. RT was eluted with 20 volumes of a gradient from 50 mM to 1 M KCl in buffer B. The individual fractions were analyzed for RT activity. The fraction containing peak RT activity was dialyzed against storage buffer (40 mM Tris-HCl, pH 8.0, 50% glycerol, 0.01% Triton X-100, 0.1 mM EDTA, 1 mM DTT, 0.1 M KCl). The purified RTs were more than 95% pure, as judged by SDS-PAGE. The protein concentrations were determined by using the Biorad calorimetric kit.

3 NTP Assay Method. Procedures were modified from those of Preston, B. D., et al. Science 242:1168 (1988). The DNA template-primer was prepared by annealing a 47-mer template (5'-GAGTTACAGTGTTTTGTTCCAGTCTG-TAGCAGTGTGTGAATGGAA G-3') (SEQ ID NO: 1) to an 18-mer primer (5'-CTTCCATTCACACACTGC-3') (SEQ ID NO: 2) $[^{32}P]$-labeled at the 5'-end with T4 polynucleotide kinase (template:primer, 3:1). Assay mixture (10 μl) contained 5 nM template-primer, 50–200 nM RT as specified in figure legends, 3 or 4 dNTPs (250 μM each), 50 mM Tris-HCl (pH 8.3), 75 mM KCl, 3 mM $MgCl_2$, 10 mM DTT. Reactions were incubated at 37° C. for 30 min and terminated by the addition of 5 μl of 40 mM EDTA, 99% formamide. Reaction products were denatured by incubating at 95 for 5 min and analyzed by electrophoresis on urea 6% polyacrylamide gels.

To determine if any TdT activity was occurring in the control reaction of the 3 dNTP assay, which uses all 4 dNTPs, was repeated with varying amounts of enzyme, >600 units to 20 units, at 37° C. for 30 min. For SS II, T197E, and Y133A, 200, 100, 50, and 20 units were used. For F309N, 646, 200, 50, 20 units were used.

Results

Figure 4:
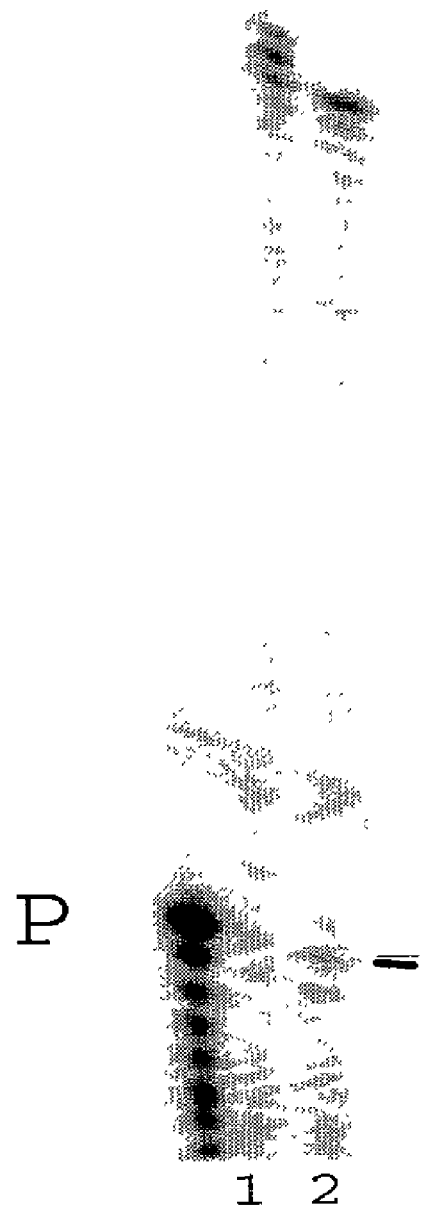
FIG. 4 represents a scanned phosphoimage of an extension assay using (1) SuperScript II RT, and (2) F309N. The [$^{32}$P]-labeled 18-mer primer annealed to a 47-mer DNA template (5 nM) was extended by equal units of RT at 37° C. for 30 minutes as seen in the extension reactions with all 4 nucleotides. The extension reactions were analyzed by denaturing 6% gel electrophoresis. P, non-extended primer.
Figure 5:
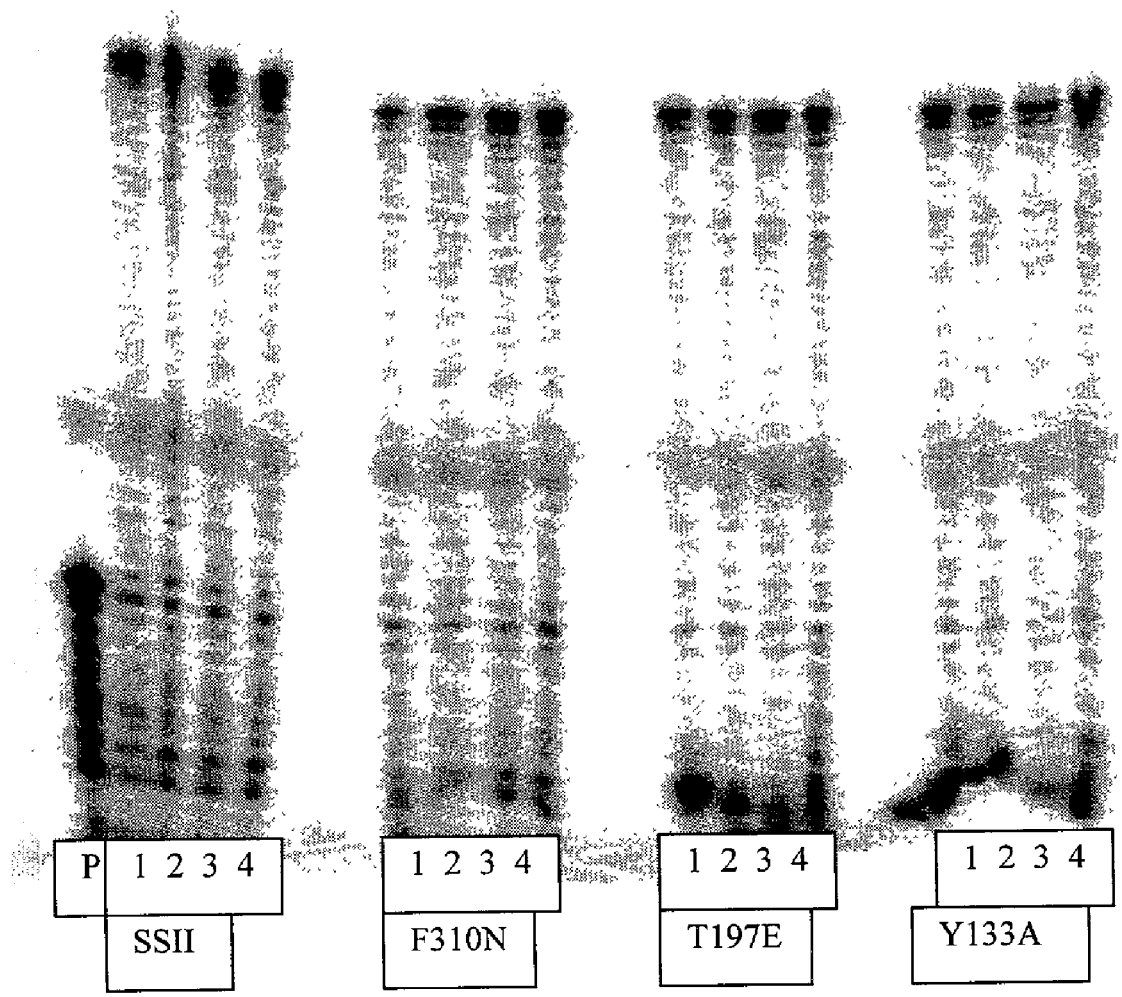
FIG. 5 represents a scanned phosphoimage showing a TdT extension assay of Superscript™ II (SS II) RT and the mutants F309N, T197E and Y133A. The [$^{32}$P]-labeled 18-mer primer annealed to a 47-mer DNA template (5 nM) was extended with decreasing units of RT (see Methods) at 37° C. for 30 min with all four nucleotides. The extension reactions were analyzed by denaturing 6% gel electrophoresis. In this assay, extension past the 47 nucleotide templates is considered non-template directed addition or TdT activity. P, non-extended primer.

We carried out a misinsertion assay of F309N (H204R, T306K) SuperScript II RT, hereafter referred to as F309N, with DNA template. This assay was employed to compare the misincorporation capability of the mutant to Superscript II. The assay is a primer extension assay using synthetic DNA template-primer and biased dNTP pools containing only three of four dNTPs. The reactions are displayed on a gel in FIG. 4. While conducting this procedure to screen for mutants with lower misensertion/misextension rates it was observed that SS II RT extended 2–3 nucleotides past the template end and that some mutations reduced or appeared to eliminate this non-template directed extension or TdT activity. As shown in FIG. 4, in the presence of all 4 dNTPs, SuperScript II RT and the mutant F309N were able to extend the primer approximately equally, with SS II RT adding 2 nucleotides past the template, and F309N adding none beyond the end of the template. To further evaluate this non-templated directed extension the control reaction for the 3 dNTP misextension assay containing all 4 dNTPs was carried out with SS II, F309N, T197E, and Y133A RT for 30 minutes with varying amounts of enzyme. The three mutants had shown very reduced levels of TdT activity in prior screens. Since it had been observed that 5 minutes with 20 units of enzyme was more than enough time for the primer extension to be completed, a 30 minute incubation and 200 to 646 units of RT were both in large excess over what was necessary for the reaction to be completed. As seen in FIG. 5, all the RT reactions at the lowest amount tested had similar extension products to the reactions at the highest unit concentrations demonstrating that the reaction had gone to completion. SS II RT added 2 nucleotides past the end of the template, F309N and T197E did not extend past the end of the template, and Y133A appears to have a small amount of product that is 1 nucleotide past the end of the template.

Example 4

Dual Thermostable and TdT Mutants

The F309 amino acid position in M-MLV reverse transcriptase (RT) aligns with the W266 position in HIV reverse transcriptase. This position is at the base of the thumb domain and is considered part of the minor groove binding tract which interacts with the minor groove of the template-primer. The mutations H204R and T306K have been shown to increase the thermostability of the enzyme. These mutations are described in U.S. Application No. 60/207,197, filed May 26, 2000, the disclosure of which is incorporated herein by reference in its entirety. The F309N mutation in an H204R/T306K clone displays 2.3× lower mutation frequency in a lacZ forward assay (Table 3) on RNA template and shorter extension products in a 3 dNTP extension assay than SuperScript II RT or H204R/T306K in SuperScript II RT. Both findings support the claim of an enzyme with higher fidelity (Table 4).

TABLE 3

Mutation Frequency of M-MLV RT High Fidelity Mutants

| Construct | total plaques | mutant plaques | MF ($\times 10^{-4}$) |
|---|---|---|---|
| SSII | 15689 | 87 | 39 |
| SSII (H204R, T306K) | 14410 | 83 | 41 |
| SSII (H204R, T306K, F309N) | 11623 | 39 | 17 |
| SSII (H204R, T306K, F309N, V223H) | 11415 | 39 | 14 |

Table 3. The mutation frequency of Superscript II RT and point mutants. Mutation frequency (MF) was determined by dividing the number of mutant plaques (light blue or white) by the total number of plaques. The background mutant frequency of the starting DNA was $17 \times 10^{-4}$ for the first 3 constructs and $20 \times 10^{-4}$ for the last construct.

TABLE 4

Error Rates of M-MLV RT High Fidelity Mutants

|  | M-MLV | SuperScript II | F309N | V223H/F309N |
|---|---|---|---|---|
| Overall ER (oER) Mismatch | 1/17,000 | 1/15,000 | 1/34,000 | 1/41,000 |
| % of total ER (mER) Frameshift | 46<br>1/37,000 | 35<br>1/42,000 | 68<br>1/50,000 | 72<br>1/58,000 |
| % of total ER (rER) Strand Jump | 46<br>1/37,000 | 60<br>1/25,000 | 21<br>1/162,000 | 22<br>1/188,000 |
| % of total ER (jER) | 8<br>1/213,000 | 5<br>1/297,000 | 11<br>1/324,000 | 6<br>1/690,000 |

Methods

Mutagenesis. Using a standard site directed mutagenesis protocol, as described in Example 3, a primer containg the V223H mutation was annealed to single strand DNA of SuperScript II with the following mutations: H204R, T306K, F309N. The colonies were sequenced to confirm the new combination of V223H, H204R, T306K, and F309N.

Selecting Colonies Containing Active RT. Colony selection was performed as in Example 3.

Purification of RT mutants. Purification was performed as in Example 3.

Sequencing of plaques. The plaques from the lacZ forward assay were transferred from the soft agar plate to Whatmann 3MM paper and allowed to dry for at least 1 hour. The plaque was then punched out and the plaque/paper disk was added directly to a sequencing reaction mix containing 4–8 μl ABI PRISM Dye Terminator Cycle Sequencing Ready Reaction (Perkin Elmer) 1 μl primer (GAA-GATCGCACTCCAGCCAGC) (SEQ ID NO: 3) and distilled water to 20 μl total volume. The ABI cycle sequencing protocol was used for 96° C. 10 seconds, 50° C. 5 seconds, 60° C. 4 minutes for 25 cycles. The paper disks were removed and the reactions were precipitated, then resuspended in loading dye and run on an ABI 377 sequencing machine.

The sequences were compared to wild type lacZ alpha sequence and then classified as frame shift (either 1 nucleotide insertion or deletion), mismatch, or strand jump (an insertion or deletion between repeated sequences). The overall error rate for each class was determined by dividing the mutation frequency by the number of detectable sites (i.e., sites the alteration of which results in a phenotypic change) (116) multiplied by 0.5 (to exclude the original single strand contribution) and then multiplied by the percentage of mutants observed to be in each class. ER=MF/(detectable sites *0.5)*(% in each class).

3dNTP assay method. 3dNTP assays were performed as in Example 3.

Results

Figure 6:
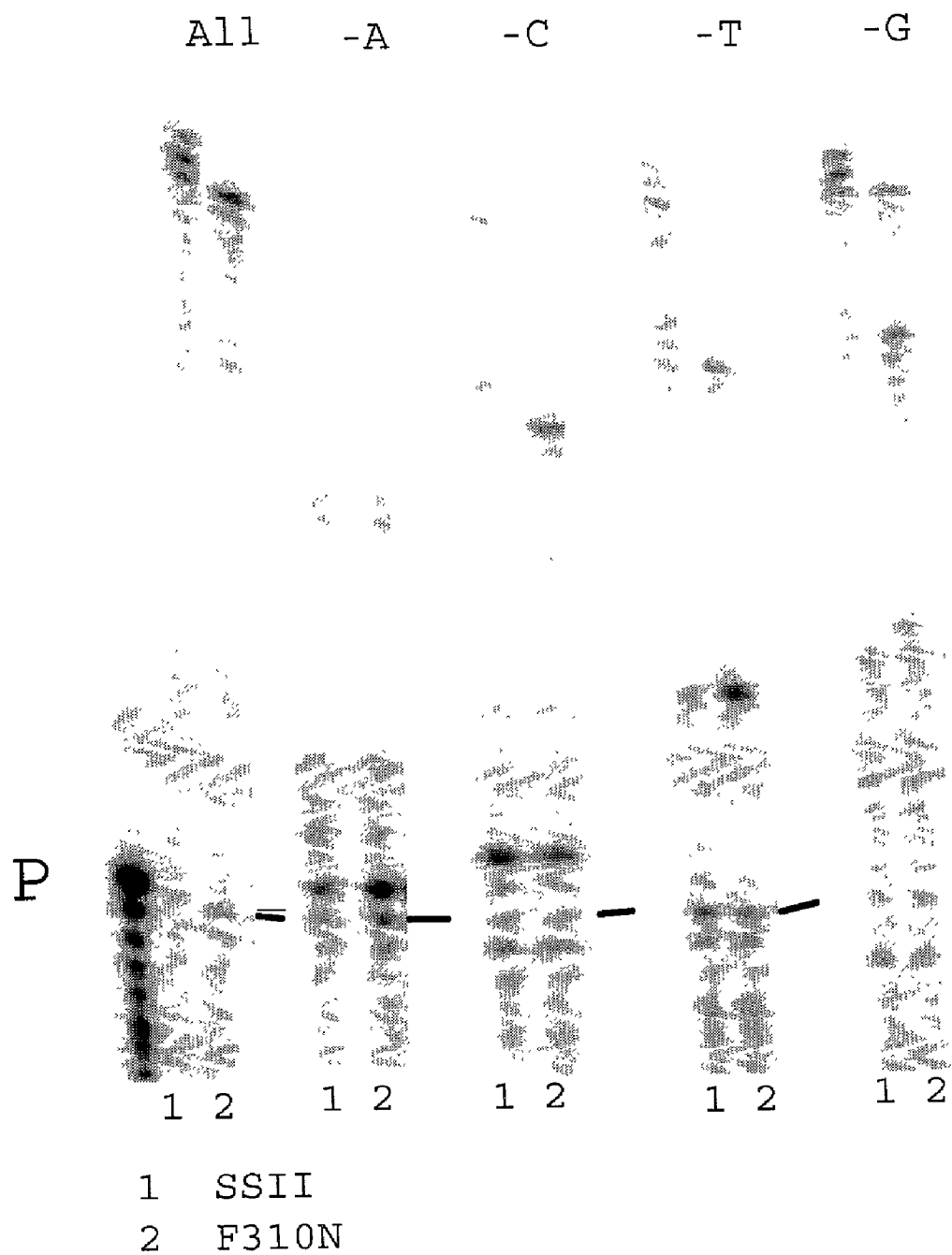
FIG. 6 represents a scanned phosphoimage showing misinsertion assays of SuperScript II RT (1) and mutant protein F309N RT (2) with DNA template. The [$^{32}$P]-labeled 18-mer primer annealed to a 47-mer DNA template (5 nM) was extended by equal units of RT protein at 37° C. for 30 min as seen in the extension reactions with all four nucleotides. The extension reactions were also performed in the presence of only 3 complementary dNTPs; minus dCTP, minus dATP, minus TTP, and minus dGTP. The extension reactions were analyzed by denaturing 6% gel electrophoresis. In this assay, the higher efficiency of elongation of terminated primer with only three nucleotides will reflect the lower fidelity of the SuperScript II RT assayed. P, non-extended primer.
Figure 7:
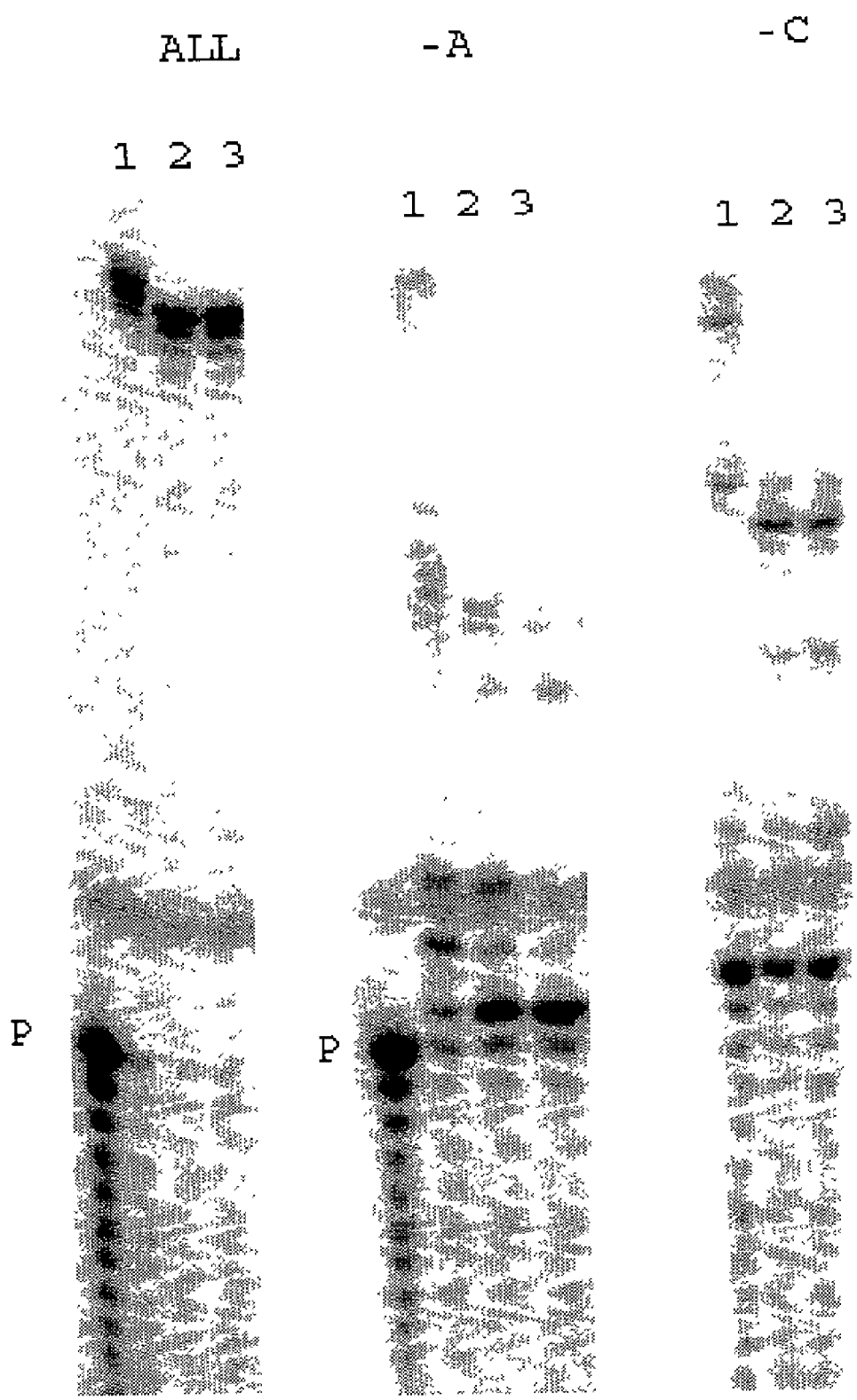
FIG. 7 represents a scanned phosphoimage showing a misinsertion assay of SuperScript II RT (1) and mutant protein T197A/F309N RT (2) and V223H/F309N with DNA template. The [$^{32}$P]-labeled 18-mer primer annealed to a 47-mer DNA template (5 nM) was extended by equal units of RT protein at 37° C. for 30 min as seen in the extension reactions with all four nucleotides. The extension reactions were also performed in the presence of only 3 complementary dNTPs; minus dATP, and minus dCTP. The extension reactions were analyzed by denaturing 6% gel electrophoresis. In this assay, the higher efficiency of elongation of terminated primer with only three nucleotides will reflect the lower fidelity of the SuperScript II RT assayed. P, non-extended primer.

We carried out a misinsertion assay of F309N (H204R T306K) SuperScript reverse transcriptase, hereafter referred to as F309N, and V223H F309N (H204R T306K), hereafter referred to as V223H/F309N with DNA template. This assay was employed to compare the misincorporation capability of the mutant to SuperScript II. The assay is a primer extension assay using synthetic DNA template-primer and biased dNTP pools containing only three of the four dNTPs. The reactions are displayed on a gel in FIG. 6 and FIG. 7. In this assay, higher efficiency of primer extension denotes lower fidelity. As shown in FIGS. 6 and 7, in the presence of all 4 dNTPs, SuperScript II RT and the mutants F309N and V223H/F309N were able to extend the primer approximately equally, with some variance in the addition of non-template directed nucleotides at the end of the primer. However when incubated with biased pools of nucleotides, SuperScript II RT was able to catalyze substantial extension past template nucleotides for which a complementary dNTP was missing, indicating use of incorrect nucleotides and lower fidelity. In FIG. 6, the F309N (2) mutant showed shorter extension products than SS II RT in each of the biased pools of three dNTPs, indicating less ability to incorporate incorrect nucleotides and thus higher fidelity. In FIG. 7, the V223H/F309N mutant was extended with just the dATP and dCTP pools. In each case V223H/F309N also had lower extension products than SuperScript II. This corresponds with the results of the lacZα assay where the F309N and V223H/F309N mutants had a lower mutation frequency than SS II RT ($17 \times 10^{-4}$ and $14 \times 10^{-4}$ to $39 \times 10^{-4}$). The RT with just the H204R T306K mutations without F309N has a mutation frequency similar to SS II RT ($41 \times 10^{-4}$ to $39 \times 10^{-4}$), suggesting that these muations do not influence fidelity. This data shows a correlation between the misinsertion assay on DNA and the lacZa assay on RNA wherein higher fidelity mutants had both shorter extension products with biased pools of dNTPs and lower mutation frequencies in the lacZa assay.

Example 5

Error Rate Determination

To determine Error Rates, mutant plaques from the lacZ forward assay were sequenced using known methods. The mutations were then classified into one of the following categories: mismatches for misinsertion events, frameshifts for single insertion or deletion events, or jumps for large insertions or deletions caused by jumping between similar sequences. An overall Error Rate was then determined for nucleic acid encoding the lacZ alpha peptide using the following equation:

ER (error rate)=MF (mutation frequency)/(number of detectable sites×0.5), where the number of detectable sites is 116.

Not all bases mutated in lacZ forward assays result in a detectable phenotypic change. To determine specific error rates for mismatch, frame shift and jumps, the mutation frequency was modified by multiplying by the percent of the total of each mutant category, and then used to determine the specific error rate. The following is a sequence map of the lacZα peptide in M13mp19 from SuperScript II RT and the high fidelity SuperScript II H203R T306K F309N reverse transcriptase assays. Underlining indicates deletions; "^" indicates insertions of the base A, T, C, or G shown above; A, T, C, or G shown above the complete sequence indicates mismatches.

Map of SuperScript II

```
                                                    T  C
         T                        T                TC  C
AGCGCAACGC AATTAATGTG AGTTAGCTCA CTCATTAGGC ACCCCAGGCT TTACACTTTA              (SEQ ID NO: 4)
                1                     1              4

CG                                 C        CC
TGCTTCCGGC TCGTATGTTG TGTGGAATTG TGAGCGGATA ACAATTTCAC ACAGGAAACA
     1

C
   CC            CG       C
GCTATG ACC ATG ATT ACG^CCA AGC TTG CAT GCC TGC AGG TCG ACT CTA GAG GAT CCC CGG
                                                            1

T                              AAAA
                                T A                             AAA
         T                      T A                               A
         T         T            T A                T            A    C
GTA CCG AGC TCG AAT TCA CTG GCC GTC GTT^TTA CAA CGT CGT GAC TGG GAA AAC CCT GGC
                                    7                            1    1    1

TTTTT
                                       TTTTT
                                    C  TTTTT
                                    C  TTT
                                    A T  T
      TC  C              C      T TC  T C T T      C     G    T
GTT ACC CAA CTT AAT CGC CTT GCA GCA CAT CCC^CCT^TTC^GCC AGC TGG CGT
                                     1     4

AAT AGC G
```

TABLE 5

| | | | |
|---|---|---|---|
| Insertions | 40 | 38% | 60% frameshift (insertion or deletion) |
| Deletions | 23 | 22% | |
| Mismatches | 36 | 35% | 35% mismatch |
| Jumps | 5 | 5% | 5% Jumps |

TABLE 6

| | | |
|---|---|---|
| Overall Error Rate (oER) | 1/15,000 | $(39 \times 10^{-4})/(116 \times 0.5)$ |
| Mismatch Error Rate (mER) | 1/42,500 | $(0.35 \times 39 \times 10^{-4})/(116 \times 0.5)$ |
| Frameshift Error Rate (fER) | 1/25,000 | $(0.60 \times 39 \times 10^{-4})/(116 \times 0.5)$ |
| Jumps Error Rate (jER) | 1/297,000 | $(0.05 \times 39 \times 10^{-4})/(116 \times 0.5)$ |

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporate by reference.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

What is claimed is:

1. A mutant MMLV reverse transcriptase comprising a polymerase domain having RNA-dependent DNA polymerase activity and a substitution in the amino acid sequence of the wild type MMLV polymerase domain within SEQ ID NO: 6, wherein amino acid number 1 of SEQ ID NO: 6 is the threonine following the initial methionine, and wherein said reverse transcriptase comprises at least one mutation at an amino acid position selected from the group consisting of Tyr64, Arg116, Lys152, Gln190, Thr197, and Phe309.

2. The reverse transcriptase of claim 1, wherein said mutation is at position Tyr64.

3. The reverse transcriptase of claim 2, wherein Tyr64 is replaced with a tryptophan.

4. The reverse transcriptase of claim 1, wherein said mutation is at position Arg116.

5. The reverse transcriptase of claim 4, wherein Arg116 is replaced with a methionine.

6. The reverse transcriptase of claim 1, wherein said mutation is at position Lys152.

7. The reverse transcriptase of claim 6, wherein Lys152 is replaced with an arginine.

8. The reverse transcriptase of claim 1, wherein said mutation is at position Gln190.

9. The reverse transcriptase of claim 8, wherein Gln190 is replaced with a phenylalanine.

10. The reverse transcriptase of claim 1, wherein said mutation is at position Thr197.

11. The reverse transcriptase of claim 10, wherein Thr197 is replaced with an alanine.

12. A mutant MMLV reverse transcriptase comprising a polymerase domain having a Val223 to His223 substitution in the amino acid sequence of the wild type MMLV polymerase domain within SEQ ID NO: 6, wherein amino acid number 1 of SEQ ID NO: 6 is the threonine following the initial methionine.

13. The reverse transcriptase of claim 1, wherein said mutation is at position Phe309.

14. The reverse transcriptase of claim 13, wherein Phe309 is replaced with asparagine.

15. The reverse transcriptase of claim 1 or 13, wherein said reverse transcriptase has substantially reduced RNase H activity.

16. The reverse transcriptase of claim 15, wherein said reverse transcriptase comprises at least one mutation at an amino acid position selected from the group consisting of Asp583, Glu562, or a combination thereof.

17. The reverse transcriptase of claim 16, wherein Asp583 is replaced with asparagine.

18. The reverse transcriptase of claim 16, wherein Glu562 is replaced with glutamine.

19. The reverse transcriptase of claim 1 or 13, further comprising at least one mutation in the RNase H domain.

20. The reverse transcriptase of claim 1 or 13 further comprising at least one mutation selected from the group consisting of Asp583, Glu 562, or a combination therof.

21. The reverse transcriptase of claim 20, wherein Asp583 is replaced with asparagine.

22. The reverse transcriptase of claim 20, wherein Glu562 is replaced with glutamine.

* * * * *